US011417813B2

(12) United States Patent
Yoda

(10) Patent No.: US 11,417,813 B2
(45) Date of Patent: Aug. 16, 2022

(54) ELECTRONIC DEVICE

(71) Applicant: SHINKO ELECTRIC INDUSTRIES CO., LTD., Nagano-ken (JP)

(72) Inventor: Atsuto Yoda, Nagano (JP)

(73) Assignee: SHINKO ELECTRIC INDUSTRIES CO., LTD., Nagano-ken (JP)

(*) Notice: Subject to any disclaimer, the term of this patent is extended or adjusted under 35 U.S.C. 154(b) by 96 days.

(21) Appl. No.: 17/093,310

(22) Filed: Nov. 9, 2020

(65) Prior Publication Data
US 2021/0143303 A1 May 13, 2021

(30) Foreign Application Priority Data

Nov. 12, 2019 (JP) .............................. JP2019-204610

(51) Int. Cl.
*H01L 33/62* (2010.01)
*H01L 25/075* (2006.01)
*H01L 27/32* (2006.01)
*F21Y 115/10* (2016.01)

(52) U.S. Cl.
CPC .......... *H01L 33/62* (2013.01); *H01L 25/0753* (2013.01); *H01L 27/3276* (2013.01); *F21Y 2115/10* (2016.08)

(58) Field of Classification Search
CPC . H01L 33/62; H01L 25/0753; H01L 27/3276; H01L 25/167; A61B 5/0059; A61B 5/02438; A61B 5/14551; A61B 2562/16; A61B 5/6838; A61B 5/6816; A61B 5/6826; A61B 2562/0233; A61B 2562/0238; F21Y 2115/10
See application file for complete search history.

(56) References Cited

U.S. PATENT DOCUMENTS

| 9,865,670 B2* | 1/2018 | Park | H01L 51/0097 |
| 10,121,988 B2* | 11/2018 | Oh | G06F 1/1652 |
| 2016/0336523 A1* | 11/2016 | Kwon | H01L 51/5293 |
| 2017/0062760 A1* | 3/2017 | Kim | H01L 27/3276 |
| 2018/0007789 A1* | 1/2018 | Kawata | H01L 51/5253 |
| 2018/0175324 A1* | 6/2018 | Fujioka | H01L 51/5253 |
| 2018/0277569 A1* | 9/2018 | Hanari | H01L 27/1218 |
| 2019/0051593 A1* | 2/2019 | Kimura | H01L 23/4985 |
| 2020/0054281 A1* | 2/2020 | Denda | A61B 5/02433 |

FOREIGN PATENT DOCUMENTS

JP 2000114728 A 4/2000

* cited by examiner

*Primary Examiner* — Kevin Quarterman
(74) *Attorney, Agent, or Firm* — Tarolli, Sundheim, Covell & Tummino LLP

(57) ABSTRACT

An electronic device includes a support body, a wiring substrate, a light emitting element, and a light receiving element. The support body includes first and second planar portions facing each other, a connecting portion connecting basal ends of the planar portions, and a receptacle. The wiring substrate is attached along an outer peripheral surface of the support body, folded at a distal end of each planar portion, and attached along an inner peripheral surface of the planar portion. The light emitting element is mounted on a first surface of the wiring substrate at a portion attached along the inner peripheral surface of the first planar portion. The light receiving element is mounted on the first surface of the wiring substrate at a portion attached along the inner peripheral surface of the second planar portion so that the light receiving element faces the light emitting element.

15 Claims, 18 Drawing Sheets

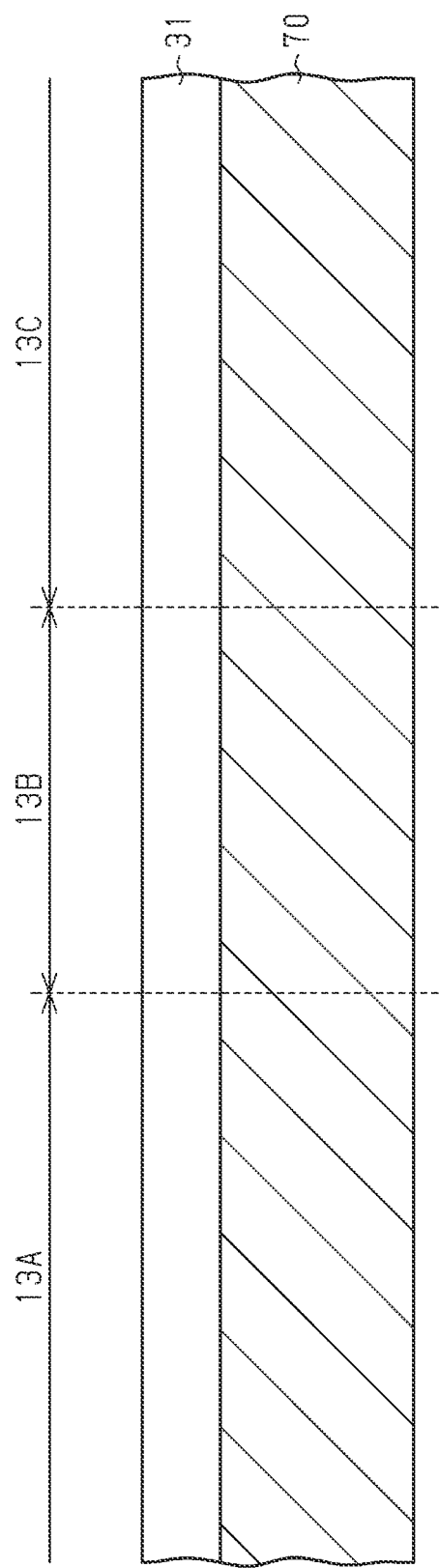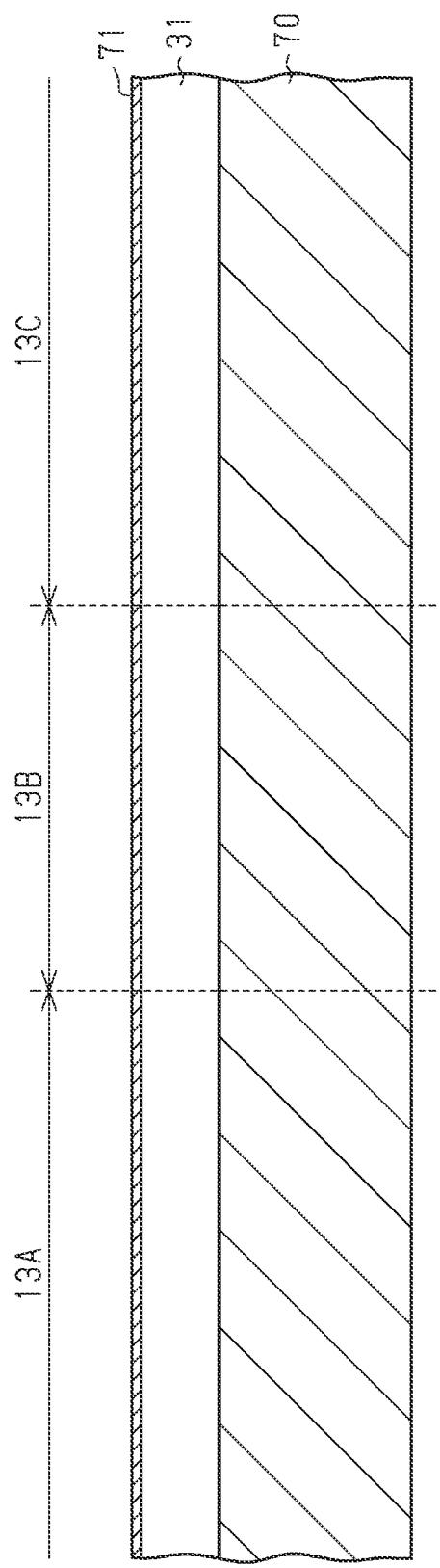

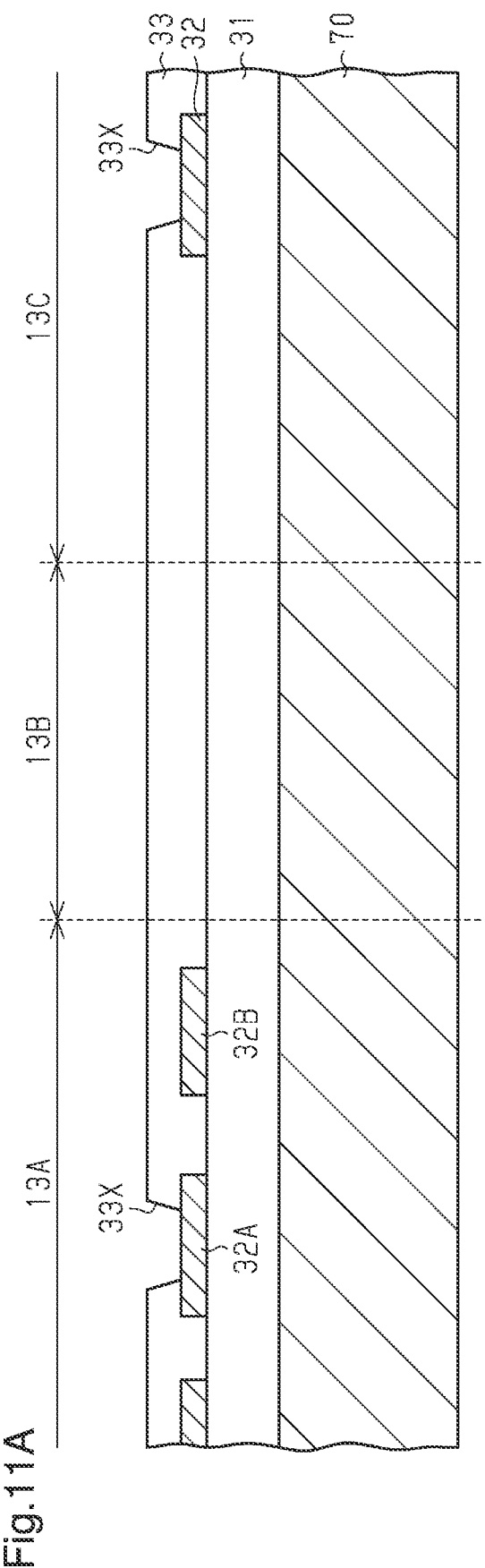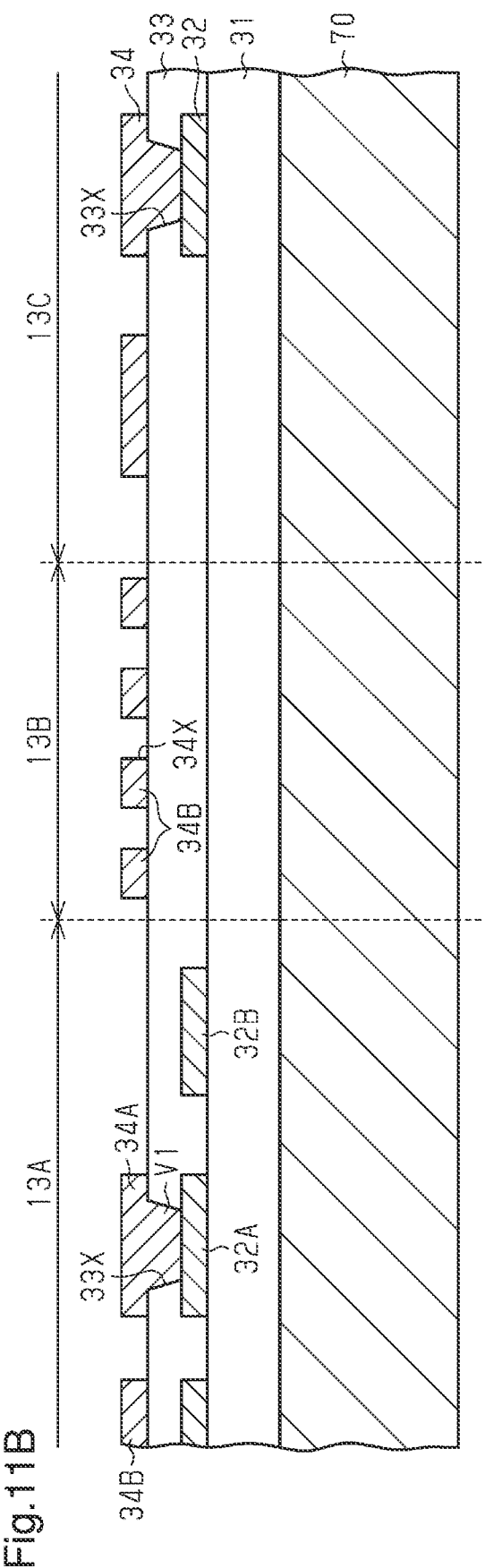

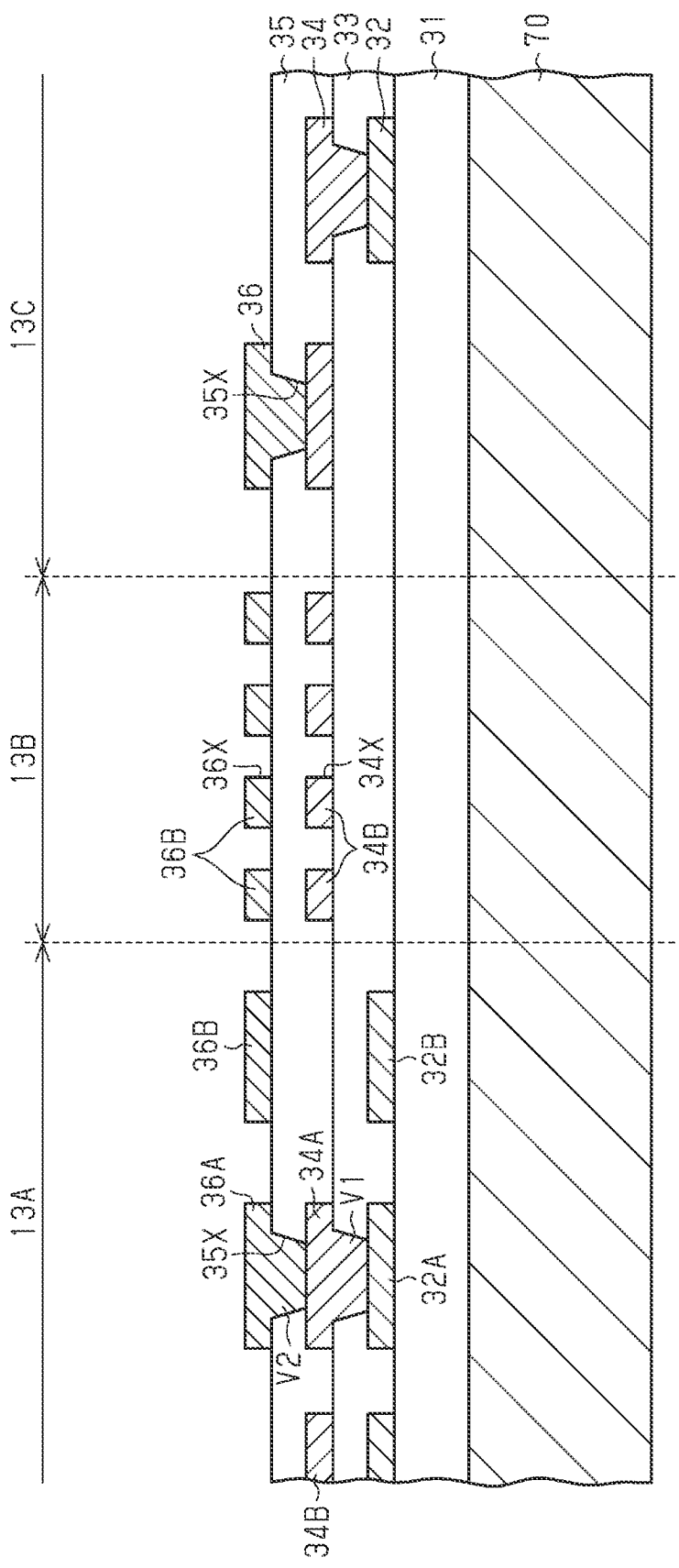

Bending Direction

Bending Direction

ELECTRONIC DEVICE

CROSS-REFERENCE TO RELATED APPLICATIONS

This application is based upon and claims the benefit of priority from prior Japanese Patent Application No. 2019-204610, filed on Nov. 12, 2019, the entire contents of which are incorporated herein by reference.

FIELD

The present disclosure relates to an electronic device.

BACKGROUND

A wiring substrate mounted on an electronic device such as a wearable terminal may be bent and used. Japanese Laid-Open Patent Publication No. 2000-114728 discloses a flexible wiring substrate. The thickness of such a wiring substrate is decreased to increase the flexibility.

As electronic devices are slimmed further, there is an increasing demand for reduction in the thickness of the wiring substrate. However, reduction in the thickness of the wiring substrate decreases the mechanical strength of the wiring substrate and adversely affects the handleability of the wiring substrate during manufacturing. For example, when electronic components are mounted on opposite surfaces of a wiring substrate, it may be difficult to handle (transport) the wiring substrate.

SUMMARY

An embodiment of an electronic device includes a support body, a wiring substrate, a light emitting element, and a light receiving element. The support body includes a first planar portion and a second planar portion that are arranged facing each other, a connecting portion connecting a basal end of the first planar portion and a basal end of the second planar portion to each other, and a receptacle surrounded by the first and second planar portions and the connecting portion. The wiring substrate is attached along an outer peripheral surface of the support body, folded at a distal end of each of the first and second planar portions, and attached along an inner peripheral surface of each of the first and second planar portions. The distal end and the basal end are located at opposite sides of the planar portion. The light emitting element is mounted on a first surface of the wiring substrate at a portion of the wiring substrate attached along the inner peripheral surface of the first planar portion. The light receiving element is mounted on the first surface of the wiring substrate at a portion of the wiring substrate attached along the inner peripheral surface of the second planar portion so that the light receiving element faces the light emitting element.

BRIEF DESCRIPTION OF THE DRAWINGS

The embodiments, together with objects and advantages thereof, may best be understood by reference to the following description of the presently preferred embodiments together with the accompanying drawings in which:

FIGS. 8A, 8B, 9A, 9B, 10A, 10B, 11A, 11B, 12, 13, and 14 are schematic cross-sectional views illustrating a method for manufacturing the semiconductor device illustrated in FIGS. 4 and 5;

DESCRIPTION OF THE EMBODIMENTS

Figure 1:
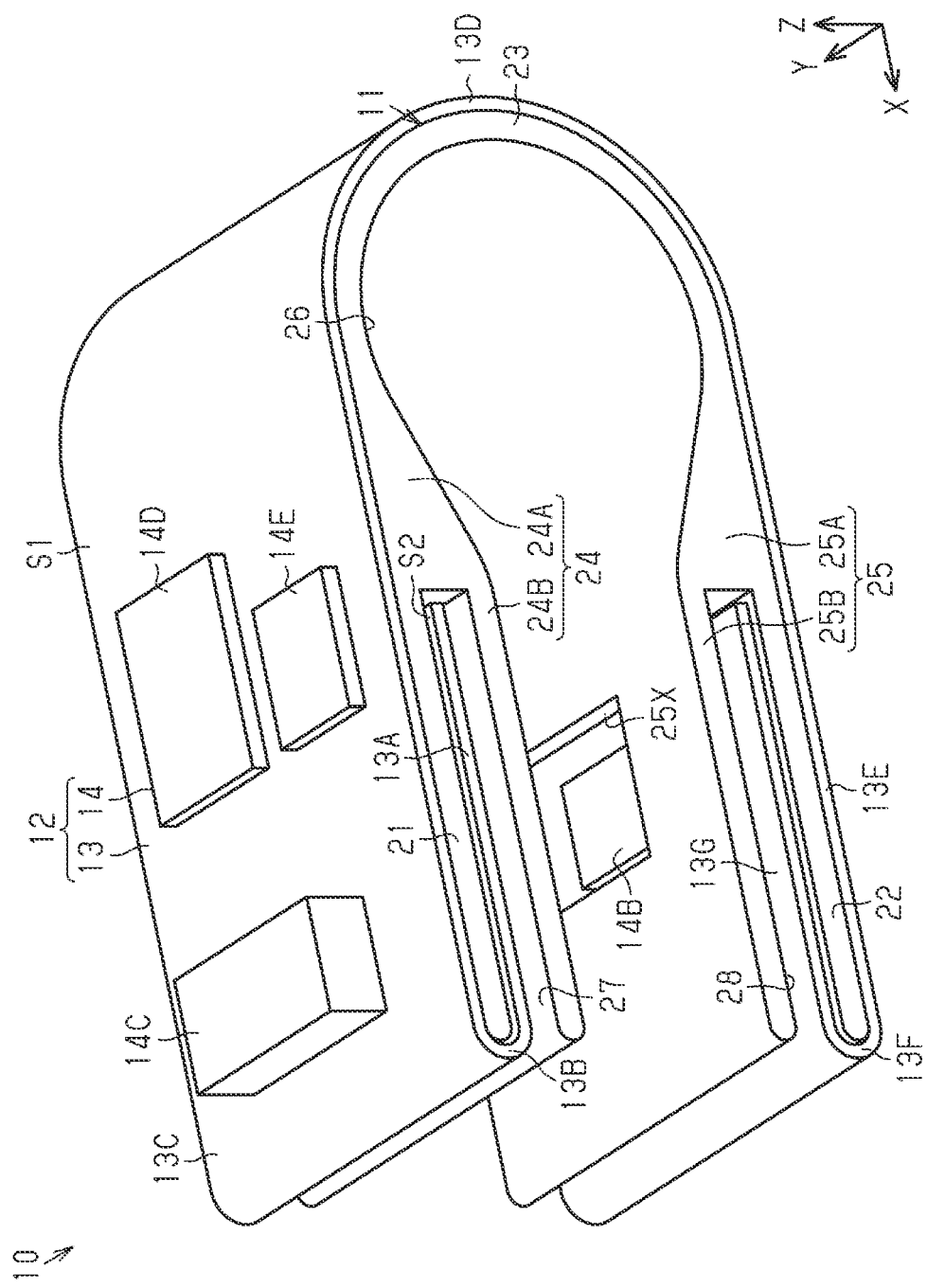
FIG. 1 is a schematic perspective view illustrating an embodiment of an electronic device.

An embodiment will be described below with reference to the accompanying drawings. Elements in the drawings may be partially enlarged for simplicity and clarity and thus have not necessarily been drawn to scale. To facilitate understanding, hatching lines may not be illustrated or be replaced by shadings in the cross-sectional drawings. The terms "parallel," "orthogonal," and "horizontal" in this specification are not limited to exactly parallel, orthogonal, and horizontal, and include generally parallel, orthogonal, and horizontal within the scope in which the advantages of the embodiment are obtained.

Structure of Electronic Device 10

As illustrated in FIG. 1, an electronic device 10 includes, for example, a support body 11 and a semiconductor device 12 attached to the support body 11. The semiconductor device 12 includes, for example, a wiring substrate 13 attached to the support body 11 and electronic components 14 mounted on the wiring substrate 13. The electronic device 10 is, for example, a biometric information measurement device (sensor device) configured to be attached to the body of an examinee and obtain biometric information of the examinee. The electronic device 10 is, for example, configured to transmit the obtained biometric information through wireless communication. The biometric information includes, for example, a blood oxygen saturation level and a pulse rate.

In FIG. 1, the x-axis indicates a front-rear direction of the electronic device 10, the y-axis indicates a width-wise direction of the electronic device 10 that is orthogonal to the x-axis, and the z-axis indicates a height-wise direction of the electronic device 10 that is orthogonal to an x, y-plane. The same applies to the x-axis, y-axis, and z-axis illustrated in the remaining drawings. In the description hereafter, for the sake of convenience, a direction extending along the x-axis is referred to as a front-rear direction X, a direction extending along the y-axis is referred to as a width-wise direction Y, and a direction extending along the z-axis is referred to as a height-wise direction Z. In addition, in the description hereafter, the direction indicated by arrow X and the direction indicated by arrow Z in FIG. 1 define frontward and upward, respectively. In this specification, "plan view" refers to a view of an object taken in the height-wise direction Z, and "planar shape" refers to a shape of an object taken in the height-wise direction Z.

Structure of Support Body 11

The support body 11 will now be described.

The support body 11 is, for example, set to have higher mechanical strengths (e.g., rigidity and hardness) than the wiring substrate 13. The support body 11 is, for example, used to support the wiring substrate 13. The support body 11 is, for example, elastic. The material of the support body 11 may be, for example, a material having a known electric permittivity. The material of the support body 11 may be, for example, a dielectric material having an electric permittivity of approximately 1 to 5. The material of the support body 11 may be, for example, an acrylic resin, polycarbonate, or an acrylonitrile butadiene styrene (ABS) resin. The support body 11 has, for example, a light blocking property. The material of the support body 11 may be, for example, a resin material dyed black or the like.

The support body 11 is, for example, U-shaped. The support body 11 has, for example, a U-shaped cross section. The support body 11 has, for example, a U-shaped side surface as viewed in the width-wise direction Y. The support body 11 has, for example, a discontinuous annular structure.

The support body 11 includes, for example, two planar portions 21 and 22 facing each other and a connecting portion 23 connecting an end of the planar portion 21 to an end of the planar portion 22. The support body 11 includes, for example, branches 24 and 25 arranged between the planar portions 21 and 22 and faced toward each other. The support body 11 is, for example, a single-piece component in which the planar portions 21 and 22, the connecting portion 23, and the branches 24 and 25 are formed integrally with each other.

In this specification, the term "facing" refers to a state in which surfaces or members are located in front of each other. The term is not limited to a state in which surfaces or members are located completely in front of each other and includes a state in which surfaces or members are located partially in front of each other. Further, in this specification, the term "facing" includes both a state in which two parts are located with another member located between the two parts and a state in which another member is not located between the two parts.

Structure of Planar Portion 21

The planar portion 21 is, for example, flat. For example, the planar portion 21 has a given thickness in the height-wise direction Z and extends in the front-rear direction X and the width-wise direction Y. The planar portion 21 extends, for example, in the front-rear direction X from an end (here, upper end) of the connecting portion 23 in the height-wise direction Z. The planar portion 21 extends, for example, straight in the front-rear direction X. The planar portion 21 extends, for example, horizontally from the upper end of the connecting portion 23 in the front-rear direction X. The planar portion 21 has, for example, a cantilever structure in which the fixed end is a basal end connected to the connecting portion 23 and the free end is a distal end located at a side opposite to the basal end in the front-rear direction X. The planar portion 21 is, for example, configured to elastically deform and bend in the height-wise direction Z.

Structure of Planar Portion 22

The planar portion 22 is, for example, flat. For example, the planar portion 22 has a given thickness in the height-wise direction Z and extends in the front-rear direction X and the width-wise direction Y. The planar portion 22 extends, for example, in the front-rear direction X from an end (here, lower end) of the connecting portion 23 in the height-wise direction Z. The planar portion 22 extends, for example, straight in the front-rear direction X. The planar portion 22 extends, for example, horizontally from the lower end of the connecting portion 23 in the front-rear direction X. The planar portion 22 extends, for example, parallel to the planar portion 21. The planar portion 22 faces, for example, the planar portion 21 in the height-wise direction Z. The planar portion 22 has, for example, a cantilever structure in which the fixed end is a basal end connected to the connecting portion 23 and the free end is a distal end located at a side opposite to the basal end in the front-rear direction X. The planar portion 22 is, for example, configured to elastically deform and bend in the height-wise direction Z.

Structure of Connecting Portion 23

Figure 2:
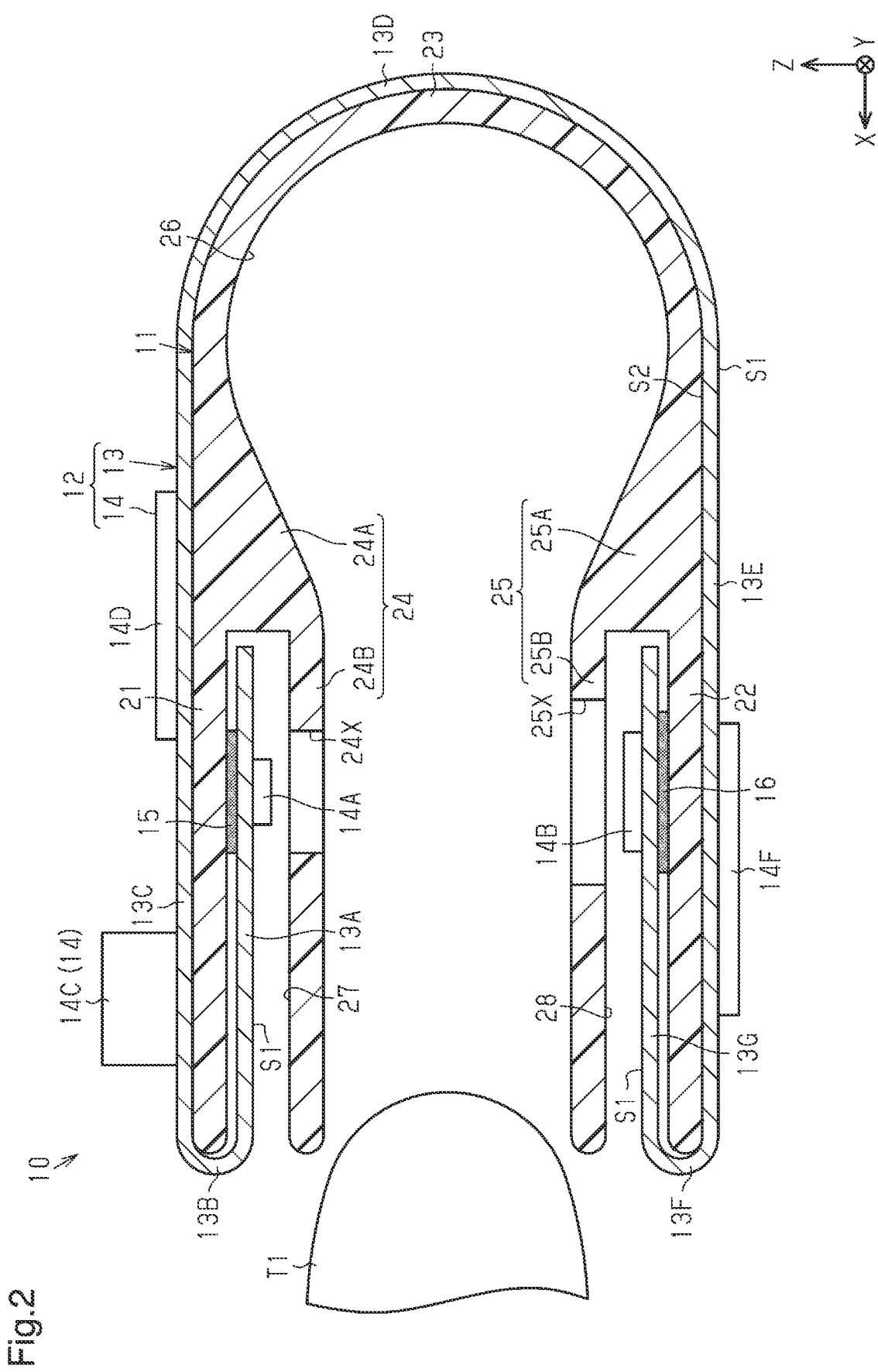
FIG. 2 is a schematic cross-sectional view of the electronic device illustrated in FIG. 1.

As illustrated in FIG. 2, the connecting portion 23, for example, connects the basal end of the planar portion 21 and the basal end of the planar portion 22. For example, the connecting portion 23 has a given thickness in the front-rear direction X and extends in the width-wise direction Y and the height-wise direction Z. The connecting portion 23 is, for example, curved as an arc or an ellipse. For example, the connecting portion 23 includes curved surfaces including an outer peripheral surface and an inner peripheral surface that are curved as an arc.

The support body 11 includes, for example, a receptacle 26 defined by the space surrounded by an inner peripheral surface (here, lower surface) of the planar portion 21, the inner peripheral surface of the connecting portion 23, and an inner peripheral surface (here, upper surface) of the planar portion 22. The receptacle 26 is configured to receive a measurement subject T1. The gap between the inner peripheral surface of the planar portion 21 and the inner peripheral surface of the planar portion 22 is set, for example, in accordance with the thickness of the measurement subject T1. The measurement subject T1 is, for example, a human body (living tissue). The human body includes, for example, a finger and an ear.

The support body 11 is, for example, configured to elastically deform and widen the gap between the planar portion 21 and the planar portion 22. That is, the support body 11 is configured to elastically deform and widen the space in the receptacle 26. For example, when the thickness of the measurement subject T1 is greater than the gap between the planar portion 21 and the planar portion 22 and the measurement subject T1 is inserted into the receptacle 26, the support body 11 elastically deforms to temporarily widen the gap between the planar portion 21 and the planar portion 22.

Structure of Branch 24

The branch 24 is arranged in the receptacle 26. The branch 24 includes, for example, a base 24A connected to the upper end of the connecting portion 23 and a plate 24B extending from the base 24A in the front-rear direction X.

The base 24A is, for example, connected to the upper end of the connecting portion 23 together with the planar portion 21. The base 24A is, for example, formed continuously and integrally with the basal end of the planar portion 21. The base 24A, for example, extends downward from the planar portion 21. The base 24A, for example, projects inside the receptacle 26 from the basal end of the planar portion 21 (the inner peripheral surface side of the planar portion 21). The base 24A has, for example, a thickness in the height-wise direction Z that is increased from the connecting portion 23 toward the plate 24B.

The plate 24B is, for example, flat. For example, the plate 24B has a given thickness in the height-wise direction Z and extends in the front-rear direction X and the width-wise direction Y. The plate 24B extends, for example, along the planar portion 21. The plate 24B extends, for example, in the front-rear direction X from an end (here, front end) of the base 24A in the front-rear direction X. The plate 24B is, for example, thinner than the front end of the base 24A. The plate 24B extends, for example, in the front-rear direction X from an end (lower end) of the base 24A in the height-wise direction Z. The plate 24B is, for example, spaced apart from the planar portion 21 by a given gap in the height-wise direction Z. The plate 24B, for example, faces the planar portion 21 in the height-wise direction Z. The planar portion 21 and the plate 24B have, for example, a biforked structure. The plate 24B extends, for example, straight in the front-rear direction X. The plate 24B extends, for example, horizontally from the lower end of the front end of the base 24A in the front-rear direction X. The plate 24B extends, for example, parallel to the planar portion 21. The plate 24B has, for example, a cantilever structure in which the fixed end is a basal end connected to the base 24A and the free end is a distal end located at a side opposite to the basal end in the front-rear direction X. The plate 24B is, for example, configured to elastically deform in a direction (here, the height-wise direction Z) in which the planar portion 21 and the planar portion 22 are arranged facing each other. The plate 24B is, for example, configured to elastically deform and bend in the height-wise direction Z.

The plate 24B includes, for example, a through hole 24X extending through the plate 24B in the thickness-wise direction (here, the height-wise direction Z). The through hole 24X is located, for example, in an intermediate portion of the plate 24B in the front-rear direction X. The planar shape of the through hole 24X is, for example, rectangular.

Structure of Branch 25

The branch 25 is arranged in the receptacle 26. The branch 25 includes, for example, a base 25A connected to the lower end of the connecting portion 23 and a plate 25B extending from the base 25A in the front-rear direction X.

The base 25A is, for example, connected to the lower end of the connecting portion 23 together with the planar portion 22. The base 25A is, for example, formed continuously and integrally with the basal end of the planar portion 22. The base 25A, for example, extends upward from the planar portion 22. The base 25A, for example, projects inside the receptacle 26 from the basal end of the planar portion 22 (the inner peripheral surface side of the planar portion 22). The base 25A has, for example, a thickness that is increased from the connecting portion 23 toward the plate 25B in the height-wise direction Z.

The plate 25B is, for example, flat. For example, the plate 25B has a given thickness in the height-wise direction Z and extends in the front-rear direction X and the width-wise direction Y. The plate 25B extends, for example, along the planar portion 22. The plate 25B extends, for example, in the front-rear direction X from an end (here, front end) of the base 25A in the front-rear direction X. The plate 25B is, for example, thinner than the front end of the base 25A. The plate 25B extends, for example, in the front-rear direction X from an end (upper end) of the base 25A in the height-wise direction Z. The plate 25B is, for example, spaced apart from the planar portion 22 by a given gap in the height-wise direction Z. The plate 25B, for example, faces the planar portion 22 in the height-wise direction Z. The planar portion 22 and the plate 25B have, for example, a biforked structure. The plate 25B extends, for example, straight in the front-rear direction X. The plate 25B extends, for example, horizontally from the upper end of the front end of the base 25A in the front-rear direction X. The plate 25B extends, for example, parallel to the planar portion 22. The plate 25B is, for example, spaced apart from the plate 24B by a given gap in the height-wise direction Z. The plate 25B, for example, faces the plate 24B in the height-wise direction Z. The plate 25B has, for example, a cantilever structure in which the fixed end is a basal end connected to the base 25A and the free end is a distal end located at a side opposite to the basal end in the front-rear direction X. The plate 25B is, for example, configured to elastically deform in a direction (here, the height-wise direction Z) in which the planar portion 21 and the planar portion 22 are arranged facing each other. The plate 25B is, for example, configured to elastically deform and bend in the height-wise direction Z.

The plate 25B includes, for example, a through hole 25X extending through the plate 25B in the thickness-wise direction (here, the height-wise direction Z). The through hole 25X is located, for example, in an intermediate portion of the plate 25B in the front-rear direction X. The through hole 25X, for example, overlaps the through hole 24X in plan view. The planar shape of the through hole 25X is, for example, rectangular. The planar shape of the through hole 25X is, for example, larger than the planar shape of the through hole 24X.

The support body 11 includes an accommodation portion 27 defined by the space surrounded by the inner peripheral surface of the planar portion 21, a front surface of the base 24A, and an upper surface of the plate 24B. The accommodation portion 27 accommodates part of the wiring substrate 13. The gap between the inner peripheral surface of the planar portion 21 and the upper surface of the plate 24B may be set to, for example, approximately 2 mm to 3 mm. The support body 11 includes an accommodation portion 28 defined by the space surrounded by the inner peripheral surface of the planar portion 22, a front surface of the base 25A, and a lower surface of the plate 25B. The accommodation portion 28 accommodates part of the wiring substrate 13. The gap between the inner peripheral surface of the planar portion 22 and the lower surface of the plate 25B may be set to, for example, approximately 2 mm to 3 mm.

Figure 3:
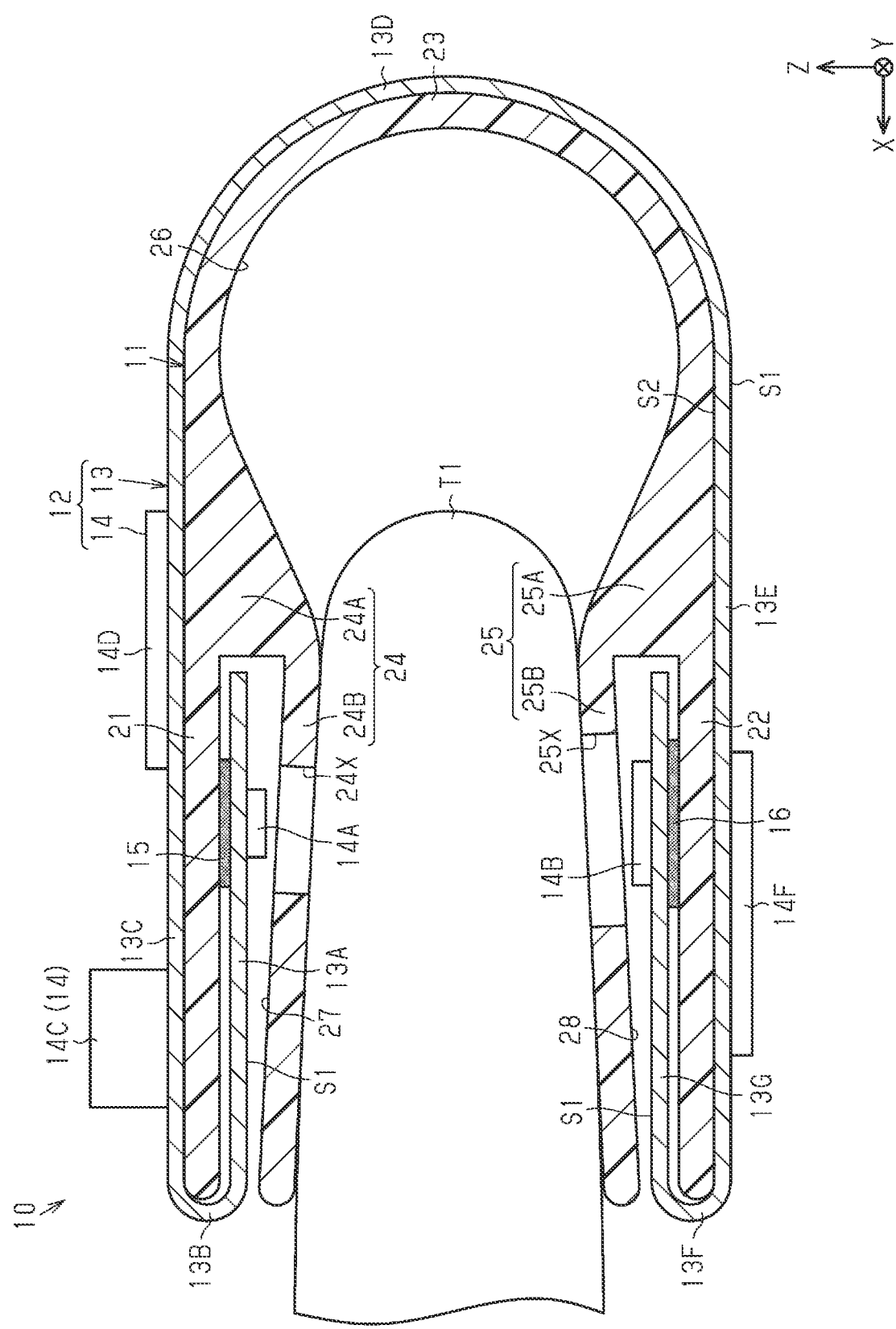
FIG. 3 is a schematic cross-sectional view of the electronic device into which a measurement subject is inserted.

As illustrated in FIG. 3, the support body 11 is, for example, configured to elastically deform and widen the gap between the plate 24B and the plate 25B. For example, when the thickness of the measurement subject T1 is greater than the gap between the plate 24B and the plate 25B and the measurement subject T1 is inserted into the receptacle 26, the support body 11 elastically deforms to temporarily widen the gap between the plate 24B and the plate 25B.

Structure of Wiring Substrate 13

The structure of the wiring substrate 13 will be described. The wiring substrate 13 is a flexible substrate having flexibility. Flexibility refers to a property capable of bending and warping.

As illustrated in FIG. 2, the wiring substrate 13 includes, for example, a mount portion 13A, a bent portion 13B, a mount portion 13C, a non-mount portion 13D on which the electronic components 14 are not mounted, a mount portion 13E, a bent portion 13F, and a mount portion 13G. In the wiring substrate 13, for example, the mount portion 13A, the bent portion 13B, the mount portion 13C, the non-mount portion 13D, the mount portion 13E, the bent portion 13F, and the mount portion 13G are formed continuously and integrally with each other. In this specification, a "bent portion" of the wiring substrate 13 is a portion of the wiring substrate 13 that is folded approximately 180 degrees.

Figure 4:
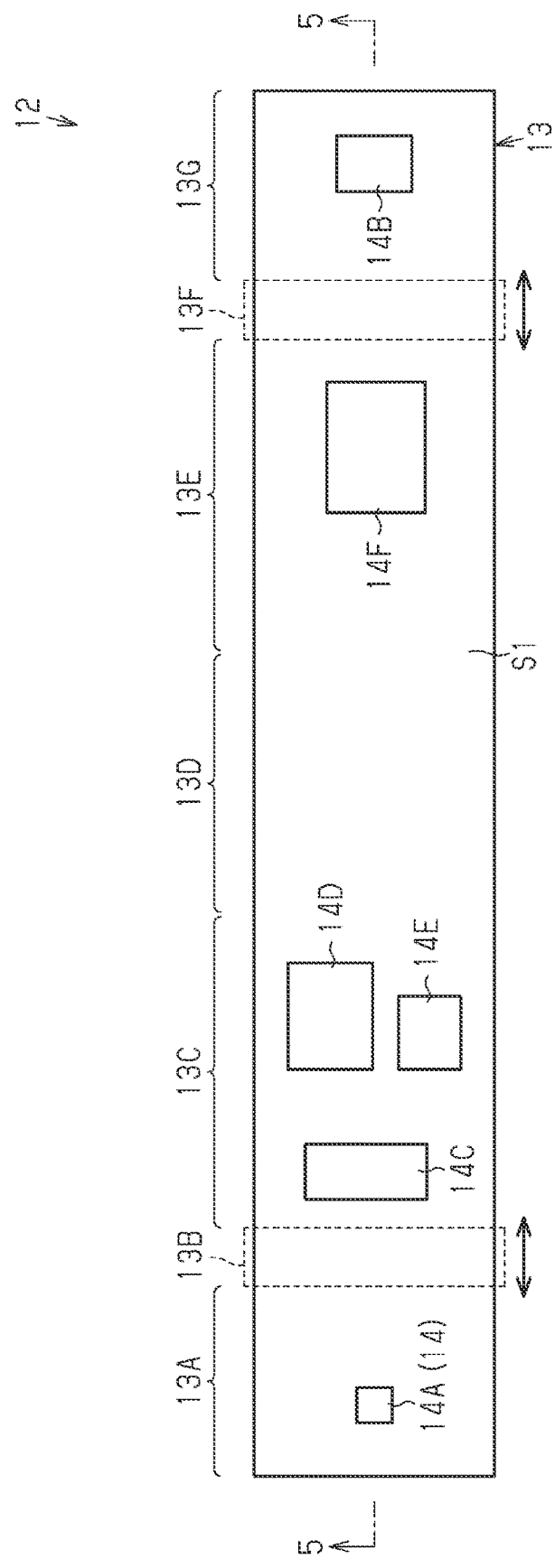
FIG. 4 is a schematic plan view illustrating an embodiment of a semiconductor device.

As illustrated in FIG. 4, the mount portion 13A, the bent portion 13B, the mount portion 13C, the non-mount portion 13D, the mount portion 13E, the bent portion 13F, and the mount portion 13G are arranged next to one another in this order in a longitudinal direction of the wiring substrate 13

(sideward direction in FIG. 4). FIG. 4 is a plan view of the semiconductor device 12 that is not attached to the support body 11, that is, the semiconductor device 12 in a state before the wiring substrate 13 is bent at the bent portions 13B and 13F. FIG. 4 is a plan view of the semiconductor device 12 as a first surface S1 (upper surface in FIG. 5) of the wiring substrate 13 is viewed from above.

Figure 5:
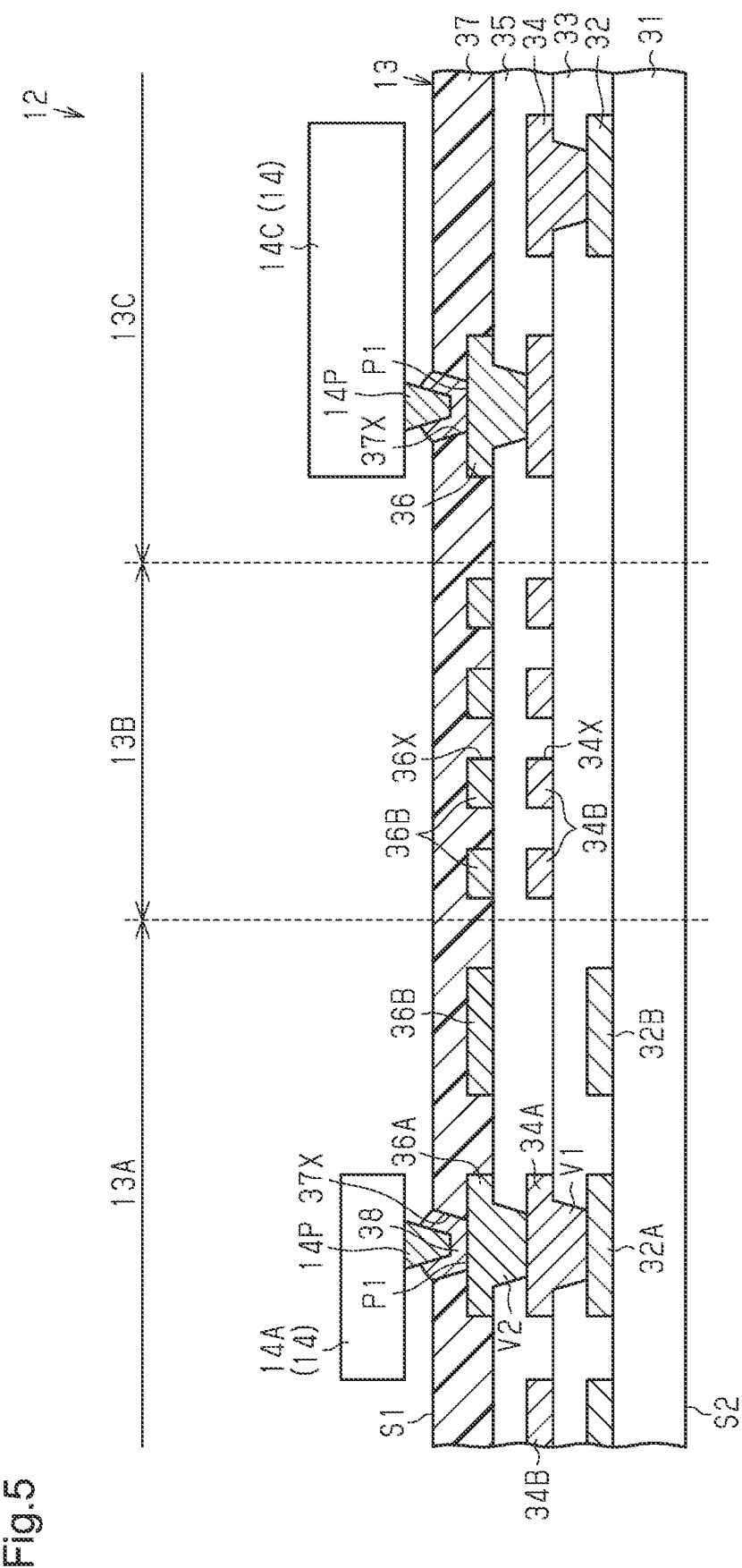
FIG. 5 is a schematic partial cross-sectional view of the semiconductor device taken along line 5-5 in FIG. 4.

As illustrated in FIG. 5, the wiring substrate 13 includes the first surface S1 (here, upper surface) and a second surface S2 (here, lower surface), and the electronic components 14 are mounted on only the first surface S1 of the wiring substrate 13. That is, the electronic components 14 are not mounted on the second surface S2 of the wiring substrate 13.

As illustrated in FIG. 4, the electronic components 14 include, for example, a light emitting element 14A mounted on the mount portion 13A and a light receiving element 14B mounted on the mount portion 13C. The light emitting element 14A is a photoelectric element and converts an electric signal into an optical signal. The light emitting element 14A may be, for example, a light emitting diode (LED). The light emitting element 14A includes, for example, LEDs that generate two different wavelengths. The light emitting element 14A includes, for example, a red LED that generates red light having a wavelength in a red region and an infrared LED that generates infrared light having a wavelength in an infrared region. The light receiving element 14B is a photoelectric element and converts an optical signal into an electric signal. The light receiving element 14B receives light emitted from the light emitting element 14A and generates an electric signal corresponding to the optical intensity of the received light. The light receiving element 14B may be, for example, a photo diode (PD) or a silicon photodiode. The light receiving element 14B may be, for example, a PD that is photoresponsive to a wavelength in the red region and a wavelength in the infrared region.

The electronic components 14 include, for example, an antenna 14C mounted on the mount portion 13C, electronic components 14D and 14E mounted on the mount portion 13C, and an electronic component 14F mounted on the mount portion 13E. The antenna 14C is used, for example, for wireless communication. The antenna 14C, for example, transmits transmission information including biometric information to an external device through wireless communication. The electronic components 14D and 14F may include, for example, a controller 50 (refer to FIG. 7) that controls the light emitting element 14A and the light receiving element 14B. The electronic component 14F includes, for example, an analog-digital (A/D) conversion circuit 52 (refer to FIG. 7) that converts an analog signal output from the light receiving element 14B into a digital signal. The electronic component 14E may include, for example, a communicator 55 (refer to FIG. 7) that transmits transmission information including biometric information to the antenna 14C. The electronic components 14D, 14E, and 14F are each, for example, a single IC chip or a module including multiple IC chips.

In the wiring substrate 13 of the present embodiment, the mount portion 13A, on which the light emitting element 14A is mounted, is arranged at one end in the longitudinal direction of the wiring substrate 13, and the mount portion 13G, on which the light receiving element 14B is mounted, is arranged at the other end in the longitudinal direction of the wiring substrate 13. In the wiring substrate 13 of the present embodiment, the electronic component 14F, which includes the A/D conversion circuit 52 (refer to FIG. 7) converting an analog signal output from the light receiving element 14B into a digital signal, is mounted on the mount portion 13E located in the vicinity of the light receiving element 14B.

The bent portions 13B and 13F are, for example, designed assuming that the bent portions 13B and 13F will be bent in a given direction. The bent portion 13B is, for example, designed assuming that the bent portion 13B will be bent in a direction in which the mount portion 13A, the bent portion 13B, and the mount portion 13C are arranged (refer to arrows illustrated in FIG. 4). The bent portion 13F is, for example, designed assuming that the bent portion 13F will be bent in a direction in which the mount portion 13E, the bent portion 13F, and the mount portion 13G are arranged (refer to arrows illustrated in FIG. 4). When including the bent portions 13B and 13F having such configurations, the wiring substrate 13 is readily bent 180 degrees at the bent portions 13B and 13F. The bending direction of the bent portions 13B and 13F conforms to the longitudinal direction of the wiring substrate 13. For example, the electronic components 14 are not mounted on the bent portions 13B and 13F.

The non-mount portion 13D connects, for example, the mount portions 13C and 13E located adjacent to each other. The non-mount portion 13D is, for example, arranged in a central portion in the longitudinal direction of the wiring substrate 13. For example, the electronic components 14 such as the light emitting element 14A, the light receiving element 14B, the antenna 14C, and the electronic components 14D, 14E, and 14F are not mounted on the non-mount portion 13D.

The structure of the semiconductor device 12 that is attached to the support body 11 will be described with reference to FIG. 2.

The wiring substrate 13 is attached to the support body 11 along the surface of the support body 11. The wiring substrate 13 is attached to the support body 11, for example, along an outer peripheral surface (here, upper surface) of the planar portion 21, the outer peripheral surface of the connecting portion 23, and an outer peripheral surface (here, lower surface) of the planar portion 22. The wiring substrate 13 is folded from the outer peripheral surface of the planar portion 21 toward the inner peripheral surface of the planar portion 21 at a distal end of the planar portion 21. In the present example, the wiring substrate 13 is bent approximately 180 degrees by the bent portion 13B and folded from the outer peripheral surface of the planar portion 21 toward the inner peripheral surface of the planar portion 21 at the distal end of the planar portion 21. In the same manner, the wiring substrate 13 is folded from the outer peripheral surface of the planar portion 22 toward the inner peripheral surface of the planar portion 22 at a distal end of the planar portion 22. In the present example, the wiring substrate 13 is bent approximately 180 degrees by the bent portion 13F and folded from the outer peripheral surface of the planar portion 22 toward the inner peripheral surface of the planar portion 22 at the distal end of the planar portion 22.

The mount portion 13A is, for example, inserted into the accommodation portion 27. The mount portion 13A covers the inner peripheral surface of the planar portion 21. The mount portion 13A is, for example, adhered to the inner peripheral surface of the planar portion 21 by an adhesive 15. The adhesive 15 is, for example, located at a position that does not overlap the antenna 14C in plan view. The adhesive 15 is, for example, located at only a position that overlaps a mount region of the light emitting element 14A in plan view. In this specification, "the mount region of the light emitting element 14A" refers to a region that is slightly larger than the region in which the light emitting element 14A is mounted.

The mount portion 13A is, for example, spaced apart from the plate 24B by a given gap in the height-wise direction Z. The light emitting element 14A is mounted on the first surface S1 of the mount portion 13A facing the planar portion 22. The light emitting element 14A faces the inner peripheral surface of the planar portion 22. The light emitting element 14A is, for example, arranged to overlap the through hole 24X in the plate 24B and the through hole 25X in the plate 25B in plan view. The light emitting element 14A is, for example, spaced apart from the plate 24B by a given gap in the height-wise direction Z. The second surface S2 of the mount portion 13A faces the inner peripheral surface of the planar portion 21.

The bent portion 13B covers, for example, a distal surface of the distal end of the planar portion 21. The bent portion 13B is, for example, curved as an arc. The bent portion 13B is, for example, folded to be U-shaped. The second surface S2 of the bent portion 13B faces the distal surface of the distal end of the planar portion 21.

The mount portion 13C covers, for example, the outer peripheral surface of the planar portion 21. The antenna 14C and the electronic component 14D are mounted on the first surface S1 of the mount portion 13C. The antenna 14C is, for example, located at a position that overlaps the plate 24B in plan view. The antenna 14C is, for example, located at a position that does not overlap the light emitting element 14A in plan view. The second surface S2 of the mount portion 13C faces the outer peripheral surface of the planar portion 21.

The non-mount portion 13D covers, for example, the outer peripheral surface of the connecting portion 23. The non-mount portion 13D is, for example, curved along the outer peripheral surface of the connecting portion 23. The second surface S2 of the non-mount portion 13D faces the outer peripheral surface of the connecting portion 23.

The mount portion 13E covers, for example, the outer peripheral surface of the planar portion 22. The electronic component 14F is mounted on the first surface S1 of the mount portion 13E. The second surface S2 of the mount portion 13E faces the outer peripheral surface of the planar portion 22.

The bent portion 13F covers, for example, a distal surface of the distal end of the planar portion 22. The bent portion 13F is, for example, curved as an arc. The bent portion 13F is, for example, folded to be U-shaped. The second surface S2 of the bent portion 13F faces the distal surface of the distal end of the planar portion 22.

The mount portion 13G is, for example, inserted into the accommodation portion 28. The mount portion 13G covers the inner peripheral surface of the planar portion 22. The mount portion 13G is, for example, adhered to the inner peripheral surface of the planar portion 22 by an adhesive 16. The adhesive 16 is, for example, located at only a position that overlaps a mount region of the light receiving element 14B in plan view. In this specification, "the mount region of the light receiving element 14B" refers to a region that is slightly larger than the region in which the light receiving element 14B is mounted.

The mount portion 13G is, for example, spaced apart from the plate 25B by a given gap in the height-wise direction Z. The light receiving element 14B is mounted on the first surface S1 of the mount portion 13G facing the planar portion 21. The light receiving element 14B faces the inner peripheral surface of the planar portion 21. The light receiving element 14B faces the light emitting element 14A. The light receiving element 14B is, for example, arranged to overlap the through hole 24X in the plate 24B and the through hole 25X in the plate 25B in plan view. The light receiving element 14B is, for example, spaced apart from the plate 25B by a given gap in the height-wise direction Z. The second surface S2 of the mount portion 13G faces the inner peripheral surface of the planar portion 22.

As illustrated in FIG. 3, the electronic device 10 is attached to the measurement subject T1 so that the measurement subject T1 is inserted into the receptacle 26. At this time, the light emitting element 14A and the light receiving element 14B face each other so that the measurement subject T1 is sandwiched to detect transmitted light of the living body. Thus, when light is emitted from the light emitting element 14A, the light is transmitted through the measurement subject T1 and received by the light receiving element 14B.

Stacking Structure of Wiring Substrate 13

The stacking structure of the wiring substrate 13 will be described with reference to FIG. 5. FIG. 5 illustrates the stacking structure in the mount portion 13A, the bent portion 13B, and the mount portion 13C. The non-mount portion 13D and the mount portions 13E and 13G illustrated in FIG. 4 have the same stacking structure as the mount portions 13A and 13C and will not be described in detail. Also, the bent portion 13F illustrated in FIG. 4 has the same stacking structure as the bent portion 13B and will not be described in detail.

As illustrated in FIG. 5, the wiring substrate 13 is a multilayer wiring substrate having a structure in which wiring layers and insulation layers are alternately stacked. The wiring substrate 13 has, for example, a structure in which an insulation layer 31, a wiring layer 32, an insulation layer 33, a wiring layer 34, an insulation layer 35, a wiring layer 36, and a solder resist layer 37 are sequentially stacked. Thus, the wiring substrate 13 of the present embodiment differs form a wiring substrate manufactured using a typical build-up process, that is, a wiring substrate in which a desired number of build-up layers is sequentially stacked on one or both of the opposite surfaces of a core substrate as a support substrate. The wiring substrate 13 of the present embodiment is a coreless substrate that does not include a support substrate.

The material of the insulation layers 31, 33, and 35 may be, for example, a flexible insulative resin having a low Young's modulus. The material of the insulation layers 31, 33, and 35 may be, for example, a non-photosensitive insulative resin including a thermosetting resin such as an epoxy resin or a polyimide resin as a main component. Also, the material of the insulation layers 31, 33, and 35 may be, for example, an insulative resin including a photosensitive resin such as a phenol resin or a polyimide resin as a main component. The insulation layers 31, 33, and 35 may include, for example, a filler such as silica or alumina. The thickness of the insulation layers 31, 33, and 35 may be, for example, approximately 20 to 45 µm.

The material of the wiring layers 32, 34, and 36 may be, for example, copper (Cu) or a copper alloy. The thickness of the wiring layers 32, 34, and 36 may be, for example, approximately 10 to 20 µm. The line-and-space (L/S) of the wiring layers 32, 34, and 36 may be, for example, approximately 10 µm/10 µm to 20 µm/20 µm. The line-and-space (L/S) shows the width of a wiring and the distance between adjacent wirings.

The insulation layer 31 is the outermost layer (here, lowermost layer) of the wiring substrate 13. In the wiring substrate 13 of the present embodiment, the lower surface of the insulation layer 31 is the second surface S2 of the wiring substrate 13. The wiring layer 32 is formed on the upper surface of the insulation layer 31. The wiring layer 32 is the lowermost wiring layer of the wiring substrate 13. The wiring layer 32 includes a wiring pattern 32A including a signal line and the like and a shield pattern 32B shielding noise such as electromagnetic noise. The shield pattern 32B is, for example, a ground pattern connected to a ground power supply (not illustrated).

The insulation layer 33 is formed on the upper surface of the insulation layer 31 to cover the wiring layer 32. The wiring layer 34 is formed on the upper surface of the insulation layer 33. The wiring layer 34 is electrically connected to the wiring layer 32 by via wirings V1 that extend through the insulation layer 33 in the thickness-wise direction. The wiring layer 34 is, for example, formed integrally with the via wirings V1. The wiring layer 34 includes a wiring pattern 34A including a signal line and the like and a shield pattern 34B shielding noise such as electromagnetic noise. The shield pattern 34B is, for example, a ground pattern connected to a ground power supply (not illustrated).

The insulation layer 35 is formed on the upper surface of the insulation layer 33 to cover the wiring layer 34. The wiring layer 36 is formed on the upper surface of the insulation layer 35. The wiring layer 36 is electrically connected to the wiring layer 34 by via wirings V2 that extend through the insulation layer 35 in the thickness-wise direction. The wiring layer 36 is, for example, formed integrally with the via wirings V2. The wiring layer 36 includes a wiring pattern 36A including a signal line and the like and a shield pattern 36B shielding noise such as electromagnetic noise. The shield pattern 36B is, for example, a ground pattern connected to a ground power supply (not illustrated).

Each of the via wirings V1 and V2 is, for example, tapered so that the width is decreased from the upper side (side close to the solder resist layer 37) toward the lower side (side close to the insulation layer 31) in FIG. 5. For example, the via wirings V1 and V2 have the form of an inverted truncated cone so that the lower surface is smaller than the upper surface. The diameter of the upper surface of the via wirings V1 and V2 may be, for example, approximately 60 to 70 µm.

The solder resist layer 37 is formed on the upper surface of the insulation layer 35 to cover the wiring layer 36. The solder resist layer 37 is the outermost layer (here, uppermost layer) of the wiring substrate 13. In the wiring substrate 13 of the present embodiment, the upper surface of the solder resist layer 37 is the first surface S1 of the wiring substrate 13. The material of the solder resist layer 37 may be, for example, an insulative resin including a photosensitive resin such as a phenol resin or a polyimide resin as a main component. The solder resist layer 37 may include, for example, a filler such as silica or alumina. The material of the solder resist layer 37 is not limited to an insulative resin including a photosensitive resin as a main component and may be, for example, the same insulative resin as used in the insulation layers 31, 33, and 35. The material of the solder resist layer 37 does not necessarily have to have a superior flexibility. When the material of the solder resist layer 37 does not have a superior flexibility, the solder resist layer 37 may be omitted from the bent portion 13B. When the solder resist layer 37 is not arranged on the bent portion 13B, the wiring layer 36 may be omitted from the bent portion 13B. The thickness of the solder resist layer 37 may be, for example, approximately 15 to 35 µm.

Openings 37X extend through the solder resist layer 37 in the thickness-wise direction and partially expose the upper surface of the wiring layer 36 as connection pads P1. The connection pads P1 are, for example, used as pads electrically connected to the electronic components 14. All of the electronic components 14 are mounted at the upper surface of the solder resist layer 37, that is, on the first surface S1 of the wiring substrate 13.

A surface-processed layer is formed on the wiring layer 36 (i.e., on the connection pads P1) exposed from the openings 37X when appropriate. Examples of the surface-processed layer include a gold (Au) layer, a nickel (Ni) layer/Au layer (metal layer formed by stacking the Ni layer and the Au layer in this order), and a Ni layer/palladium (Pd) layer/Au layer (metal layer formed by stacking the Ni layer, the Pd layer, and the Au layer in this order). The Au layer is a metal layer formed of Au or an Au alloy, the Ni layer is a metal layer formed of Ni or a Ni alloy, and the Pd layer is a metal layer formed of Pd or a Pd alloy. Each of the Ni layer, the Au layer, and the Pd layer may be, for example, a metal layer formed through an electroless plating process (electroless plated metal layer). In another example of the surface-processed layer, an organic solderability preservative (OSP) film may be formed on the surface of the connection pads P1 through an anti-oxidation process such as an OSP process. The OSP film may be a coating of an organic compound such as an azole compound or an imidazole compound.

In the wiring substrate 13 of the present embodiment, the number of wiring layers in the bent portion 13B is less than the number of wiring layers in the mount portions 13A and 13C. In the mount portions 13A and 13C and the bent portion 13B, the wiring layer 32 is located in only the mount portions 13A and 13C. That is, the wiring layer 32 is not located in the bent portion 13B. The wiring layers 34 and 36 are located in each of the mount portions 13A and 13C and the bent portion 13B. Thus, in the wiring substrate 13 of the present example, the bent portion 13B has two wiring layers, namely, the wiring layers 34 and 36, whereas the mount portions 13A and 13C have three wiring layers, namely, the wiring layers 32, 34, and 36. The configuration in which the bent portion 13B has a fewer number of wiring layers than the mount portions 13A and 13C lowers density of the wiring layers formed in the bent portion 13B and obtains a favorable flexibility.

In the present example, in the mount portions 13A and 13C and the bent portion 13B, the via wirings V1 and V2 are located in only the mount portions 13A and 13C. That is, in the present example, the via wirings V1 and V2 are not located in the bent portion 13B. Thus, the via wirings V1 and V2 are not located in the bent portion 13B, which is configured to bend. The via wirings V1 and V2 are located in only the mount portions 13A and 13C, which are not expected to be bent. When the bent portion 13B is folded 180 degrees, this configuration appropriately limits occurrence of defective conductivity resulting from separation of the via wirings V1 and V2.

The wiring patterns 32A, 34A, and 36A may be located in any of the mount portions 13A and 13C and the bent portion 13B. However, in the present example of the wiring substrate 13, the wiring layer 32 is not formed in the bent portion 13B. Accordingly, the wiring pattern 32A is not formed in the bent portion 13B.

The shield patterns 32B, 34B, and 36B may be located in any of the mount portions 13A and 13C and the bent portion 13B. However, in the present example of the wiring substrate 13, the wiring layer 32 is not formed in the bent portion 13B. Accordingly, the shield pattern 32B is not formed in the bent portion 13B. In the wiring substrate 13 of the present example, for example, the shield patterns 34B and 36B are formed in the mount portions 13A and 13C and the bent portion 13B.

In the bent portion 13B, through holes 34X and 36X respectively extend through the shield patterns 34B and 36B in the thickness-wise direction.

Structure of Shield Patterns 34B and 36B in Bent Portion 13B

The structure of the shield patterns 34B and 36B located in the bent portion 13B will now be described. The structure of the shield pattern 34B located in the bent portion 13B will be described. The shield pattern 36B located in the bent portion 13B has the same structure as the shield pattern 34B located in the bent portion 13B and will not be described in detail.

Figure 6:
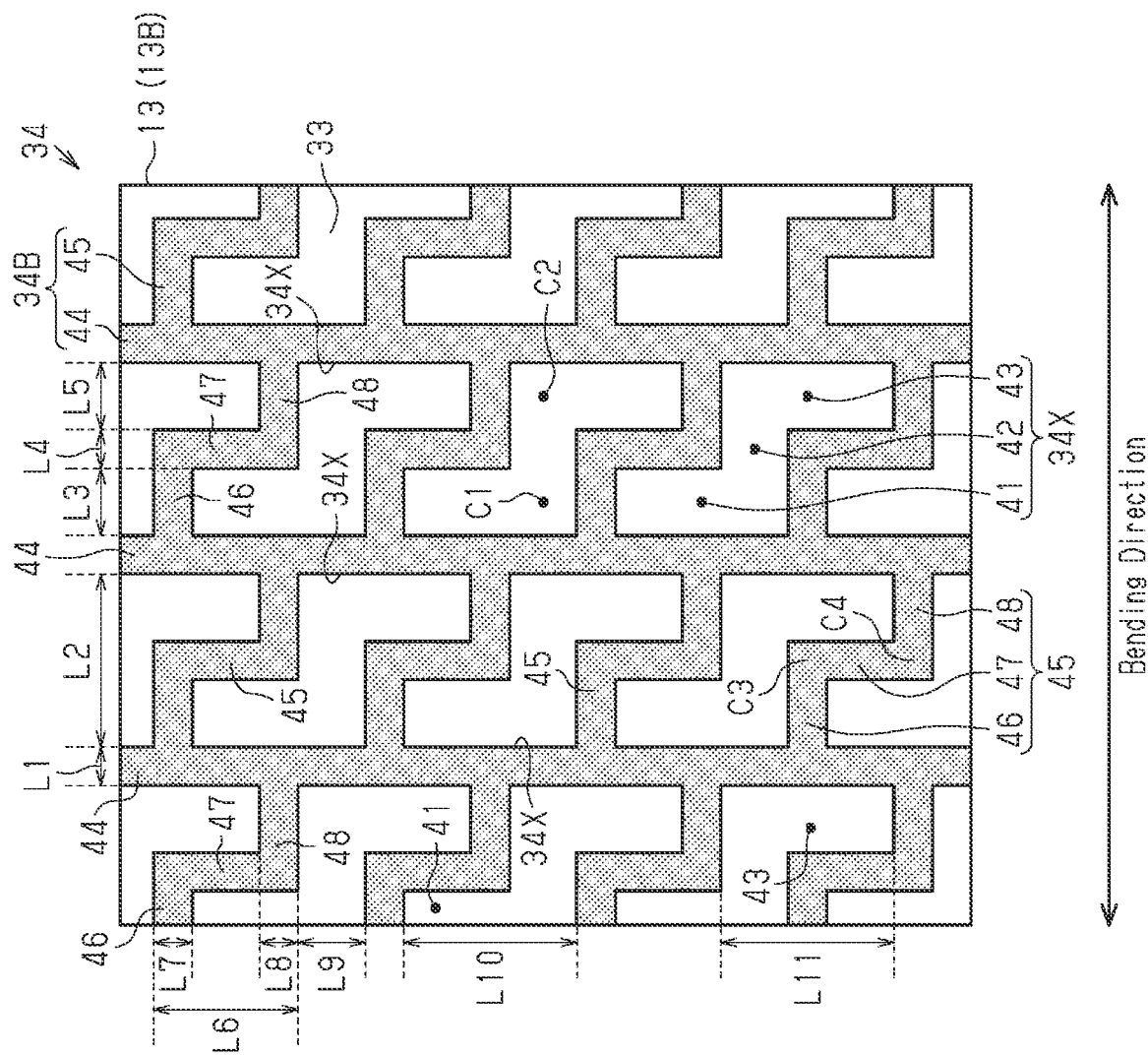
FIG. 6 is a schematic plan view illustrating a shield pattern of the wiring substrate of the embodiment.

As illustrated in FIG. 6, the shield pattern 34B located in the bent portion 13B includes the through holes 34X. The through holes 34X are arranged at given intervals. The through holes 34X are arranged, for example, at given intervals in the bending direction and also at given intervals in a direction orthogonal to the bending direction in plan view (in the present embodiment, lateral direction of the wiring substrate 13).

The planar shape of each through hole 34X includes at least one corner. In the present example, the planar shape of the through hole 34X is crank-shaped and includes two corners C1 and C2. The through hole 34X includes an opening 41 extending in the lateral direction, which is orthogonal to the bending direction, an opening 42 extending from an end of the opening 41 in the bending direction, and an opening 43 extending from an end of the opening 42 in the lateral direction and located at a position different from the opening 42. The opening 41 and the opening 43 are, for example, the same in planar shape and size. The through holes 34X are, for example, the same in planar shape and size. The through holes 34X are, for example, arranged in the same direction. The through holes 34X define the shield pattern 34B having a grid-like structure in the bent portion 13B.

The shield pattern 34B located in the bent portion 13B includes, for example, supports 44 extending parallel to each other in a given direction and joints 45 formed between adjacent ones of the supports 44 to connect the adjacent supports 44. The joints 45 are formed, for example, continuously and integrally with the supports 44.

Each support 44, for example, extends in a direction intersecting the bending direction in plan view. In the present example, the support 44 extends in a direction (here, the lateral direction of the wiring substrate 13) orthogonal to the bending direction (here, the longitudinal direction of the wiring substrate 13). For example, the support 44 has a given width and extends straight. The supports 44 are, for example, arranged at given intervals in the bending direction. In the example illustrated in FIG. 6, three supports 44 are arranged. However, the number of supports 44 is not particularly limited. Two supports 44 may be arranged, or four or more supports 44 may be arranged.

The joints 45 are, for example, arranged at given intervals in the lateral direction of the wiring substrate 13 between adjacent ones of the supports 44. The joints 45 are, for example, arranged at given intervals in the bending direction. In the present example, the joints 45 that are arranged next to one another in the bending direction are located at the same position in the lateral direction. The joints 45 are, for example, the same in planar shape and size. The joints 45 are, for example, arranged in the same direction.

The planar shape of each joint 45 includes at least one corner. In the present example, the planar shape of each joint 45 is crank-shaped and includes two corners C3 and C4. In the example illustrated in FIG. 6, each joint 45 includes an extension 46 extending in the bending direction, a connector 47 extending from an end of the extension 46 in the lateral direction, which is orthogonal to the bending direction, and an extension 48 extending from an end of the connector 47 in the bending direction. That is, in the joint 45, the connector 47 is bent substantially orthogonal to the extension 46, and the extension 48 is bent substantially orthogonal to the connector 47. In the joint 45, the corner C3 is formed in the part that connects the extension 46 and the connector 47, and the corner C4 is formed in the part that connects the connector 47 and the extension 48. In the joint 45, the extension 46 and the extension 48 are located at different positions in the lateral direction. The extension 46 and the extension 48 are, for example, the same in planar shape and size. The extension 46 has an end connected to one of the adjacent supports 44. The extension 48 has an end connected to the other one of the adjacent supports 44. For example, the adjacent supports 44, the extension 46, the connector 47, and the extension 48 are formed continuously and integrally with each other.

As described above, in the shield pattern 34B located in the bent portion 13B, the planar shape of the joint 45 located between the adjacent supports 44 includes the corners C3 and C4. As a result, the joint 45 has spring-like characteristics, and a favorable flexibility is obtained from the spring-like characteristics.

The width L1 of the support 44 (i.e., dimension of the support 44 in the bending direction) may be, for example, approximately 25 to 100 μm. The distance L2 between adjacent ones of the supports 44 in the bending direction may be, for example, approximately 225 to 400 μm. The dimension L3 of the extension 46 in the bending direction may be, for example, approximately 100 to 150 μm. The width L4 of the connector 47 (i.e., dimension of the connector 47 in the bending direction) may be, for example, approximately 25 to 100 μm. The dimension L5 of the extension 48 in the bending direction may be, for example, approximately 100 to 150 μm. The dimension L6 of the entire joint 45 in the widthwise direction (i.e., dimension of the connector 47 in the lateral direction) may be, for example, approximately 201 to 350 μm. The width L7 of the extension 46 (i.e., dimension of the extension 46 in the lateral direction) may be, for example, approximately 25 to 100 μm. The width L8 of the extension 48 (dimension of the extension 48 in the lateral direction) may be, for example, approximately 25 to 100 μm. The distance L9 between adjacent ones of the joints 45 in the lateral direction may be, for example, approximately 100 to 150 μm. The distance L10 between adjacent ones of the extensions 46 in the lateral direction (i.e., dimension of the opening 41 of the through hole 34X in the lateral direction) may be, for example, approximately 126 to 500 μm. The distance L11 between adjacent ones of the extensions 48 in the lateral direction (i.e., dimension of the opening 43 of the through hole 34X in the lateral direction) may be, for example, approximately 250 to 300 μm. The dimensions of each member described above may be appropriately set based on the shield property and the flexural modulus that the shield pattern 34B is required to have.

In the present embodiment, the width L1 of the support 44, the width L4 of the connector 47, the width L7 of the extension 46, and the width L8 of the extension 48 are set to be the same. In addition, in the present embodiment, the distance L2 between the adjacent supports 44 in the bending direction is set to be greater than the distance L10 between the adjacent extensions 46 in the lateral direction (or the distance L11 between the adjacent extensions 48 in the lateral direction). Thus, the distance between the supports 44, which have a higher rigidity than the joints 45, is relatively increased, so that a favorable flexibility is obtained.

Although the details are not illustrated in FIG. 5, the shield pattern 36B located in the bent portion 13B includes the through holes 36X that have the same planar shape as the through holes 34X. The through holes 36X are, for example, the same in size as the through holes 34X and arranged at the same intervals as the through holes 34X. In the present embodiment, the through holes 34X and 36X that are adjacent to each other in the stacking direction overlap in plan view.

Each of the shield patterns 34B and 36B located in the bent portion 13B has an area such that the shield patterns 34B and 36B maintain required shield properties. When the material of the shield patterns 34B and 36B is copper, the copper remaining rate of each of the shield patterns 34B and 36B located in the bent portion 13B may be set in any manner within a range allowing for the continuity of the required shield properties. For example, the copper remaining rate of the shield patterns 34B and 36B located in the bent portion 13B may be set to approximately 30% to 40%. The copper remaining rate refers to the rate of the area of a copper layer occupied on an insulation layer.

As illustrated in FIG. 5, the electronic components 14 include, for example, electrode terminals 14P arranged on one surface (in FIG. 5, lower surface) of the electronic components. The electrode terminals 14P may be, for example, metal posts, gold bumps, or solder bumps. The material of the metal posts may be, for example, copper or a copper alloy. The material of the solder bumps may be, for example, an alloy including lead (Pb), an alloy of tin (Sn) and Cu, an alloy of Sn and silver (Ag), or an alloy of Sn, Ag, and Cu.

In the electronic components 14, for example, the electrode terminals 14P are electrically connected to the connection pads P1 of the wiring substrate 13. The electrode terminals 14P are electrically connected to the connection pads P1 by, for example, solder 38 arranged on the connection pads P1. Thus, the electronic components 14 are electrically connected to the wiring pattern 36A of the wiring substrate 13 by the electrode terminals 14P and the solder 38. That is, the electronic components 14 are flip-chip-mounted on the wiring substrate 13. The material of the solder 38 may be, for example, an alloy including Pb, an alloy of Sn and Cu, an alloy of Sn and Ag, or an alloy of Sn, Ag, and Cu.

Electric Configuration of Electronic Device 10

The electric configuration of the electronic device 10 will now be described.

Figure 7:
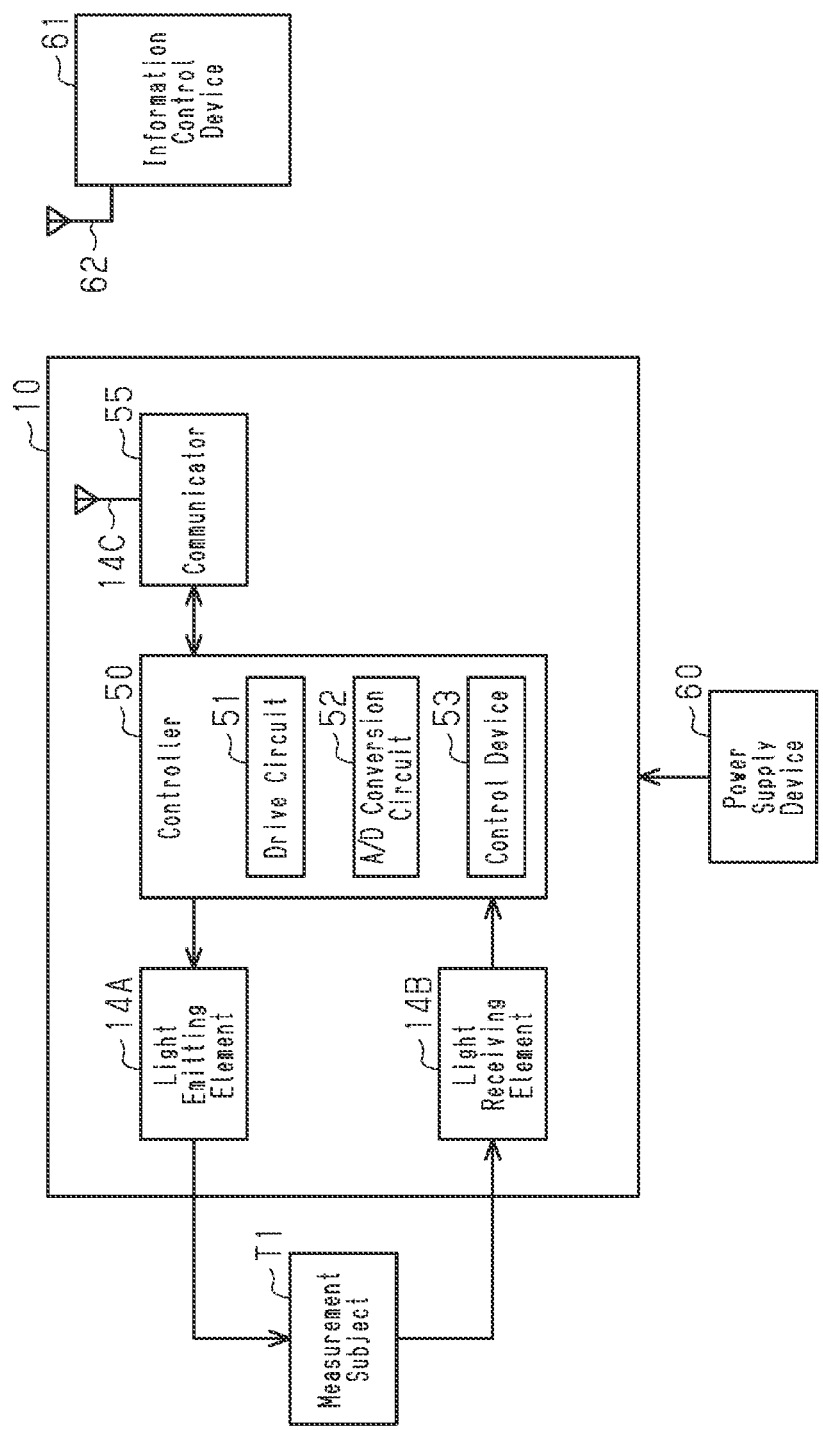
FIG. 7 is a block diagram of the electric configuration of the electronic device illustrated in FIG. 1.

As illustrated in FIG. 7, the electronic device 10 configures a biometric information measurement system, for example, in cooperation with a power supply device 60 and an information control device 61.

The electronic device 10 is actuated, for example, by power supplied from the power supply device 60. For example, the electronic device 10 is actuated by power supplied from the power supply device 60 in a contactless manner. The electronic device 10 obtains biometric information of the measurement subject T1 using, for example, the light emitting element 14A and the light receiving element 14B. For example, identification information (ID) is set in the electronic device 10. When multiple electronic devices 10 are used, identification information set in the electronic devices 10 differs between the electronic devices 10. The electronic device 10, for example, transmits transmission information including the obtained biometric information and an identification number set in the electronic device 10 through wireless communication.

The information control device 61 includes, for example, an antenna 62 and receives information transmitted from the electronic device 10. The information control device 61, for example, stores the received information in a storage device. The storage device may be, for example, a hard disk drive (HDD). The information control device 61, for example, shows the received information on a display. The information control device 61, for example, displays an analysis result, which is obtained by executing a given analysis process on the received information, on the display. The display may be, for example, a liquid crystal display or an organic electronic luminescence (EL).

The electronic device 10 includes, for example, the light emitting element 14A, the light receiving element 14B, the controller 50, and the communicator 55. The controller 50 is electrically connected to the light emitting element 14A and the light receiving element 14B. The controller 50 is electrically connected to the communicator 55.

The controller 50 includes, for example, a drive circuit 51 that drives the light emitting element 14A, the A/D conversion circuit 52 that converts an analog signal into a digital signal, and a control device 53. The drive circuit 51 is, for example, configured to execute control that causes the light emitting element 14A to emit light based on a given sampling cycle. The light emitted from the light emitting element 14A is, for example, transmitted through the measurement subject T1 inserted into the receptacle 26 (refer to FIG. 3) and received by the light receiving element 14B. The A/D conversion circuit 52, for example, obtains biometric information (analog signal) output from the light receiving element 14B in synchronization with light emission of the light emitting element 14A and converts the obtained analog signal into a digital signal. The control device 53 is, for example, configured to centrally control operation of each circuit in the controller 50. The control device 53, for example, executes a given analysis process on a digital signal (i.e., biometric information) generated in the A/D conversion circuit 52 and generates analysis result information. The control device 53, for example, transmits the digital signal (i.e., biometric information) generated in the A/D conversion circuit 52 or the analysis result information to the communicator 55.

The control device 53 may be configured to be circuitry that includes [1] one or more processors that execute various processes in accordance with computer programs (software), [2] one or more dedicated hardware circuits that execute at least some of various processes such as application specific integrated circuits (ASICs), or [3] a combination of these. The processor includes a central processing unit (CPU) and memory such as random access memory (RAM) and read only memory (ROM). The memory stores program codes or instructions configured to cause the CPU to execute processes. The memory, or a computer readable medium, includes any type of medium that is accessible by a general-purpose computer or a dedicated computer.

The communicator 55 is connected to the antenna 14C so as to communicate with the information control device 61 in accordance with a given wireless communication method.

The communicator 55 is, for example, a transmission circuit. The communicator 55 transmits transmission information including biometric information obtained by the light emitting element 14A and the light receiving element 14B and the analysis result information to the antenna 14C. The communicator 55 transmits the transmission information from the antenna 14C to the information control device 61 through wireless communication. Examples of wireless communication methods include Bluetooth low energy (BLE) (Bluetooth is registered trademark), ZigBee (registered trademark), ANT+ (registered trademark), and NFC.

Manufacturing Method of Semiconductor Device 12

The method for manufacturing the semiconductor device 12 will now be described with reference to FIGS. 8A to 14. In the present embodiment, a single semiconductor device is individually manufactured on a support substrate, and then the support substrate is removed. However, a portion that will become multiple semiconductor devices may be manufactured on a support substrate and the support substrate may be removed, and the portion may be singulated into the semiconductor devices. To facilitate understanding, portions that ultimately become elements of the semiconductor device 12 are indicated by reference characters used to denote the final elements. A structural body of the mount portions 13A and 13C and the bent portion 13B will be illustrated and described.

As illustrated in FIG. 8A, a support substrate 70 is prepared. The support substrate 70 may be, for example, a metal plate or a metal foil. In the present embodiment, for example, a copper foil is used. The thickness of the support substrate 70 may be, for example, approximately 18 to 100 μm.

Then, the insulation layer 31 is formed on the upper surface of the support substrate 70 to cover the entire upper surface of the support substrate 70. When a resin film is used as the insulation layer 31, for example, after the support substrate 70 is laminated with the resin film, the resin film may be heated under pressure at a temperature of approximately 130° C. to 190° C. so that the resin is cured to form the insulation layer 31. Alternatively, a liquid or paste of an insulative resin may be applied to the upper surface of the support substrate 70 through a spin coating process or the like, and the applied insulative resin may be heated and cured at a temperature of approximately 130° C. to 190° C. to form the insulation layer 31.

In the step illustrated in FIG. 8B, a seed layer 71 is formed on the upper surface of the insulation layer 31 to cover the entire upper surface of the insulation layer 31. The seed layer 71 may be formed, for example, through an electroless plating process (e.g., electroless copper plating method) or sputtering.

Figure 9A:
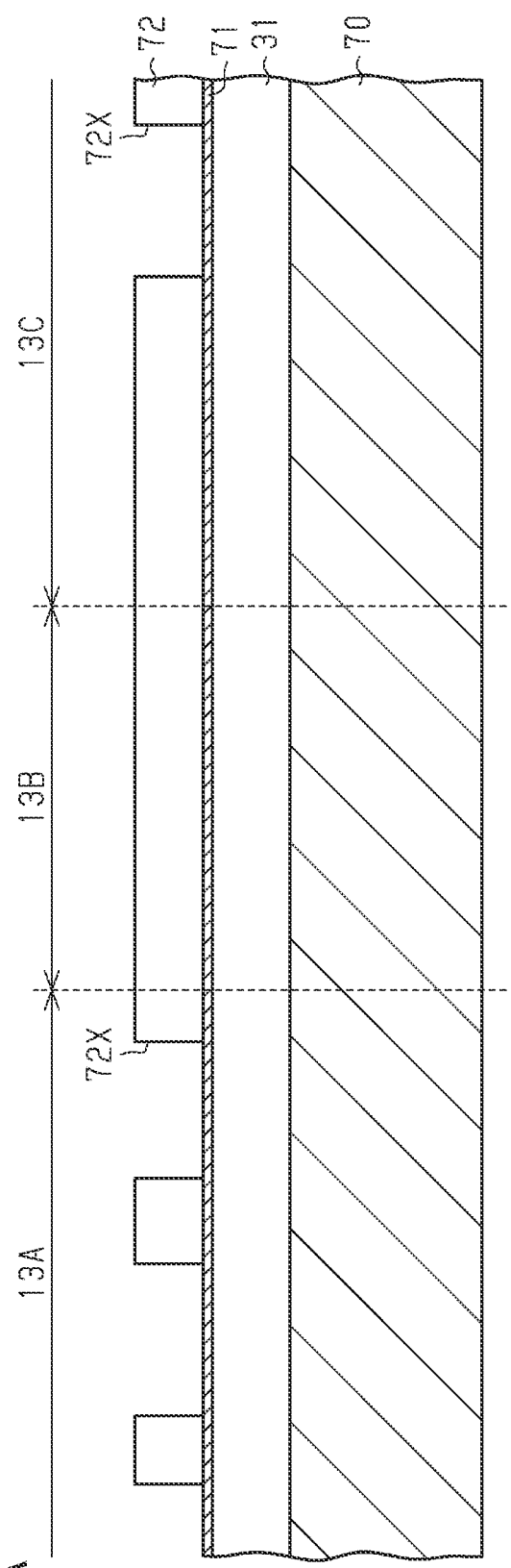

In the step illustrated in FIG. 9A, a resist layer 72 including an open pattern 72X is formed on the upper surface of the seed layer 71. The open pattern 72X exposes a portion of the upper surface of the seed layer 71 corresponding to the formation region of the wiring layer 32 (refer to FIG. 5). The material of the resist layer 72 may be, for example, a photosensitive dry film resist or a liquid photoresist (e.g., dry film resist or liquid resist of novolac resin or acrylic resin). For example, when a photosensitive dry film resist is used, the upper surface of the insulation layer 31 is laminated with a dry film through thermocompression bonding, and the dry film is patterned through photolithography to form the resist layer 72. When a liquid photoresist is used, the resist layer 72 may also be formed by the same steps.

Figure 9B:
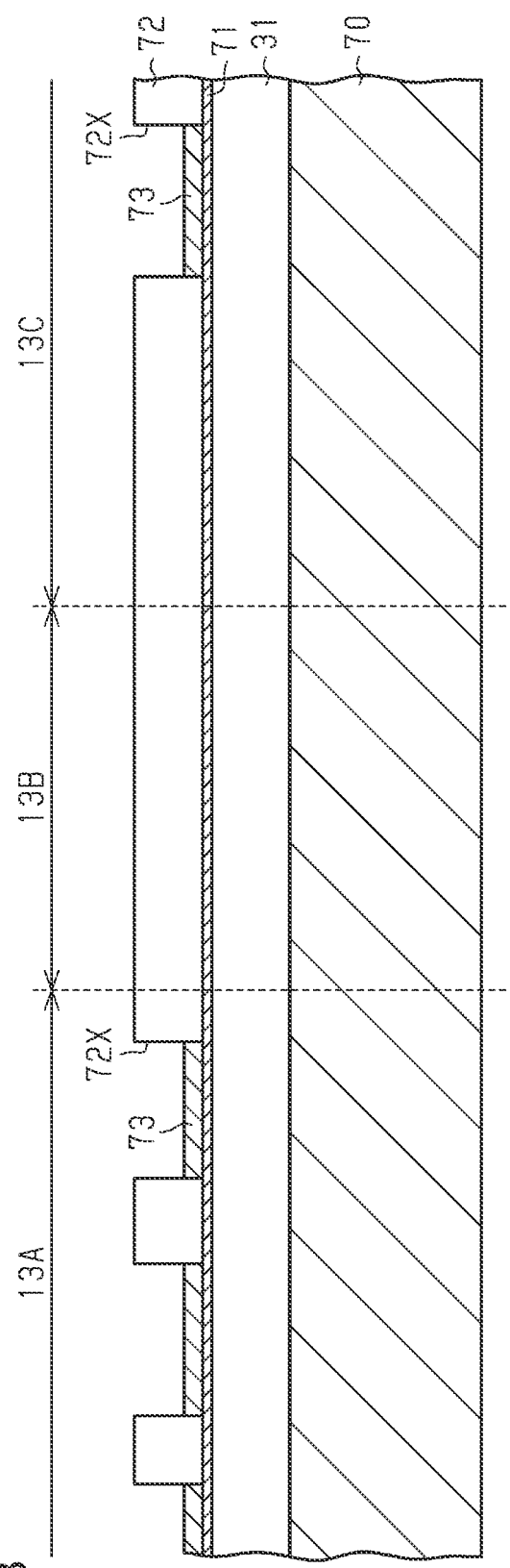

In the step illustrated in FIG. 9B, a conductive layer 73 is formed on the upper surface of the seed layer 71 exposed from the open pattern 72X in the resist layer 72. For example, as the resist layer 72 is used as a plating mask, the upper surface of the seed layer 71 exposed from the open pattern 72X undergoes an electrolytic plating process (e.g., electrolytic copper plating process) that uses the seed layer 71 as a plating power feeding layer, so that the conductive layer 73 is formed on the seed layer 71.

The resist layer 72 is removed, for example, by an alkaline stripping solution (e.g., organic amine stripping solution, caustic soda, acetone, or ethanol).

Figure 10A:
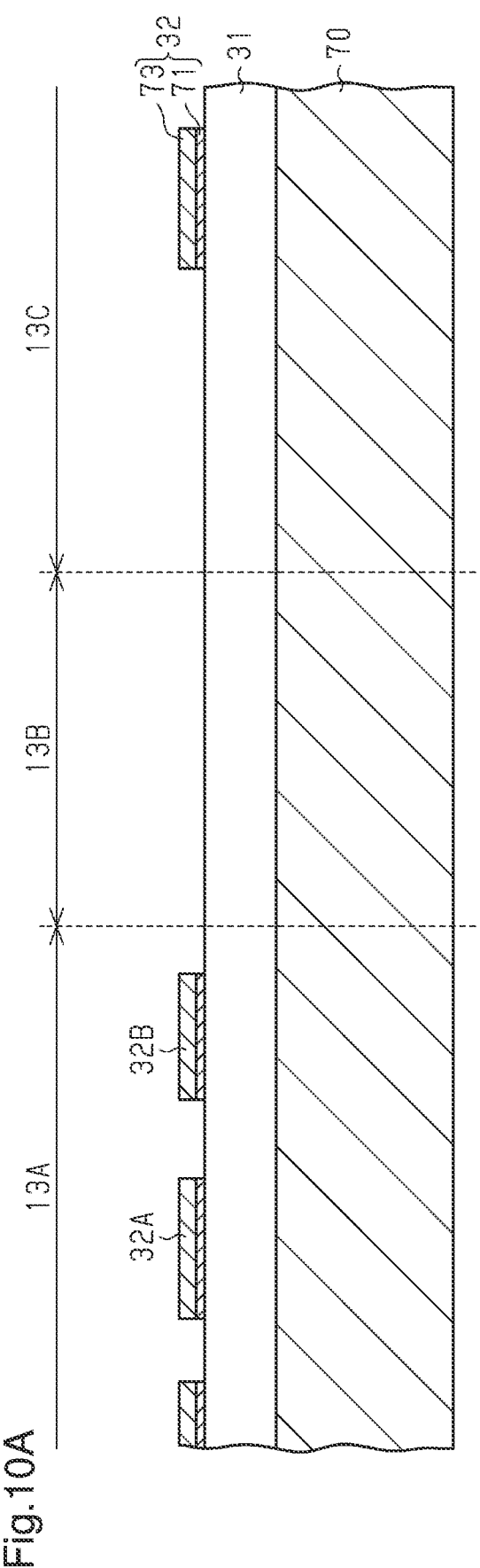

In the step illustrated in FIG. 10A, as the conductive layer 73 is used as an etching mask, an unwanted portion of the seed layer 71 is etched and removed. When the seed layer 71 is an electroless copper plated layer, for example, an unwanted portion of the seed layer 71 is removed by wet etching using a sulfuric acid-hydrogen peroxide-based etchant. As a result, the wiring layer 32 including the seed layer 71 and the conductive layer 73 is formed. The wiring layer 32 includes the wiring pattern 32A and the shield pattern 32B. However, the wiring layer 32 is not formed in the bent portion 13B. In FIGS. 10B to 14, the seed layer 71 and the conductive layer 73 are not illustrated and are illustrated as the wiring layer 32 (the wiring pattern 32A and the shield pattern 32B).

Figure 10B:
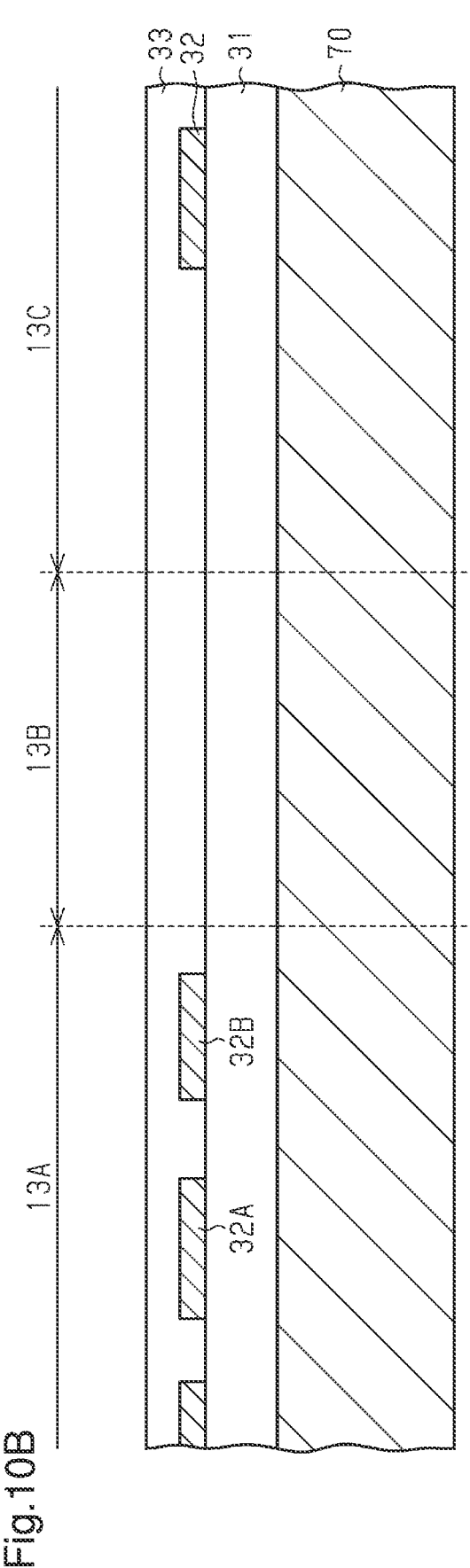

In the step illustrated in FIG. 10B, the insulation layer 33 is formed on the upper surface of the insulation layer 31 to cover the wiring layer 32. The insulation layer 33 may be formed, for example, by the same process as the insulation layer 31.

In the step illustrated in FIG. 11A, via holes 33X are formed in the insulation layer 33 to extend through the insulation layer 33 in the thickness-wise direction and partially expose the upper surface of the wiring layer 32. In the mount portions 13A and 13C and the bent portion 13B, the via holes 33X are formed in only the mount portions 13A and 13C. The via holes 33X may be formed, for example, by laser cutting using a $CO_2$ laser or a YAG laser. When the insulation layer 33 is formed of a photosensitive resin, the desired via holes 33X may be formed, for example, through photolithography.

When the via holes 33X are formed by laser cutting, a desmear process is performed to remove resin smears from the surface of the wiring layer 32 exposed in the bottom of the via holes 33X.

In the step illustrated in FIG. 11B, the via holes 33X are filled with a via conductor to form the via wirings V1, and the wiring layer 34 is formed on the upper surface of the insulation layer 33 and electrically connected to the wiring layer 32 by the via wirings V1. The via wirings V1 and the wiring layer 34 may be formed using, for example, various wiring forming processes such as a semi-additive process or a subtractive process. The wiring layer 34 includes the wiring pattern 34A and the shield pattern 34B. At this time, the shield pattern 34B located in the bent portion 13B includes the through holes 34X having the planar shape including the corners C1 and C2 (refer to FIG. 6).

In the step illustrated in FIG. 12, in the same manner as the steps illustrated in FIGS. 10B and 11A, the insulation layer 35 is formed on the upper surface of the insulation layer 33 and includes via holes 35X exposing part of the upper surface of the wiring layer 34.

In the same manner as the step illustrated in FIG. 11B, the via holes 35X are filled with a via conductor to form the via wirings V2, and the wiring layer 36 is formed on the upper surface of the insulation layer 35 and electrically connected to the wiring layer 34 by the via wirings V2. The wiring layer 36 includes the wiring pattern 36A and the shield pattern 36B. At this time, the shield pattern 36B located in the bent portion 13B includes the through holes 36X having the planar shape including the corners C1 and C2 (refer to FIG. 6).

Figure 13:
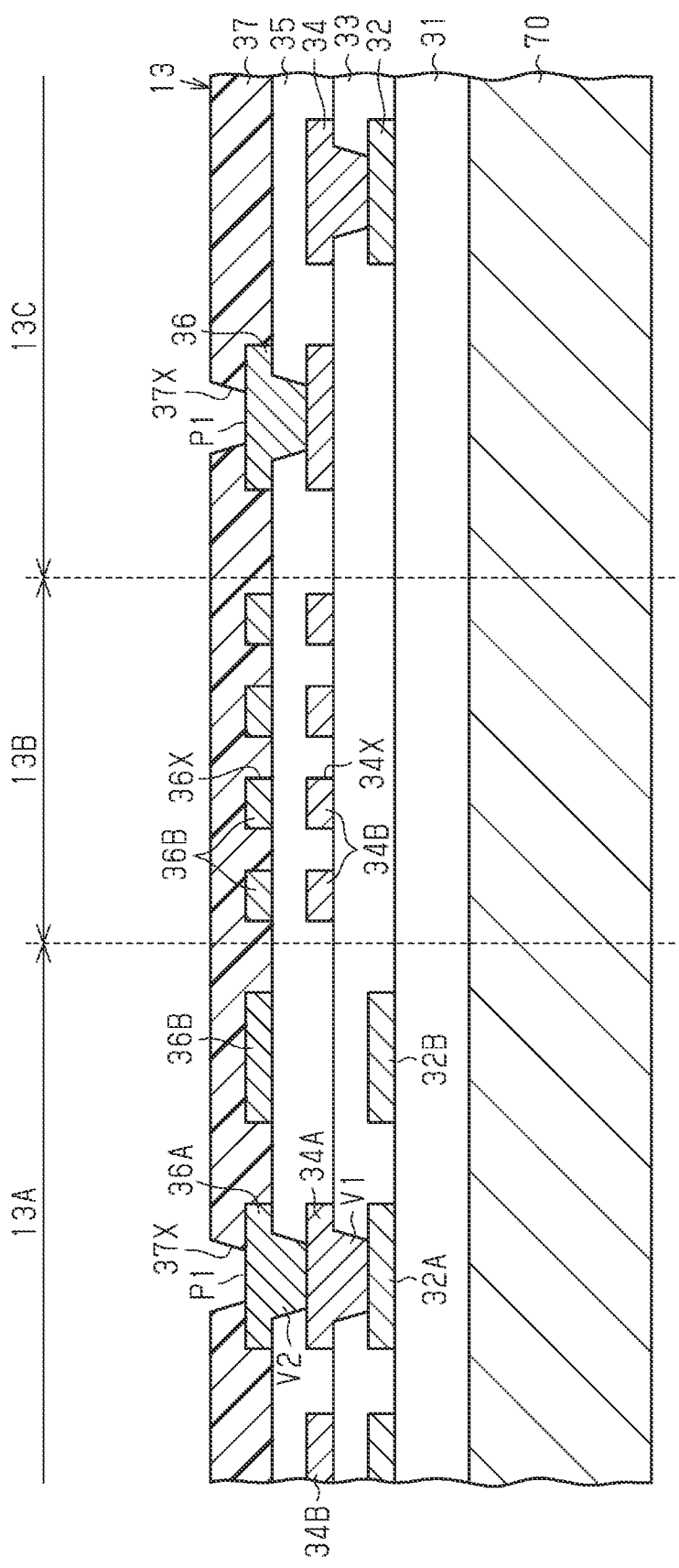

In the step illustrated in FIG. 13, the solder resist layer 37 is formed on the upper surface of the insulation layer 35. The solder resist layer 37 includes the openings 37X exposing part of the upper surface of the wiring layer 36 as the connection pads P1. The solder resist layer 37 may be formed, for example, by laminating a photosensitive solder resist film or applying a liquid solder resist and patterning the resist through photolithography. A surface-processed layer may be formed on the connection pads P1 when appropriate.

The steps described above manufacture the wiring substrate 13 on the support substrate 70.

Figure 14:
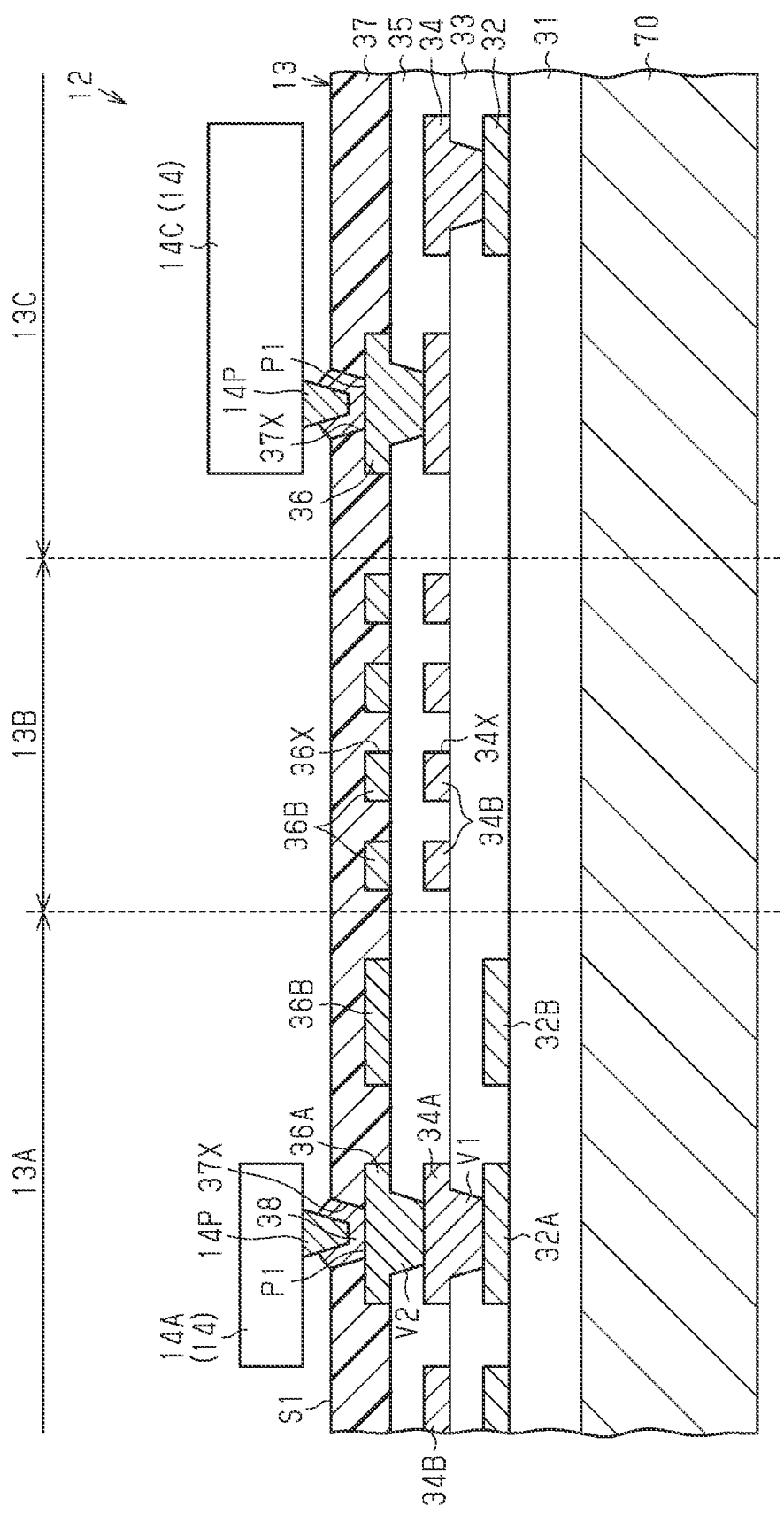

In the step illustrated in FIG. 14, the electronic components 14 are mounted on the wiring substrate 13. The solder 38 is formed on the connection pads P1 exposed from the openings 37X. The solder 38 may be formed by, for example, applying a solder paste. The electrode terminals 14P of the electronic components 14 are positioned on the connection pads P1 of the wiring substrate 13. The solder 38 is melted to electrically connect the electrode terminals 14P of the electronic components 14 to the connection pads P1. As a result, the electronic components 14 are flip-chip-mounted on the wiring substrate 13.

The steps described above manufacture the semiconductor device 12 on the support substrate 70. In the semiconductor device 12 of the present embodiment, all of the electronic components 14 are mounted on one surface (here, first surface S1) of the wiring substrate 13. Therefore, before the support substrate 70 is removed, all of the electronic components 14 are mounted on the wiring substrate 13. The electronic components 14 are mounted on the wiring substrate 13 having a mechanical strength that is increased by the support substrate 70. This improves handleability of the wiring substrate 13 and the semiconductor device 12 during the manufacturing process.

Subsequently, the support substrate 70 is removed so that the semiconductor device 12 illustrated in FIGS. 4 and 5 is manufactured. When a copper foil is used as the support substrate 70, the support substrate 70 may be removed, for example, by wet etching that uses a ferric chloride aqueous solution, a cupric chloride aqueous solution, or an ammonium persulfate aqueous solution.

The present embodiment has the advantages described below.

(1) The light emitting element 14A is mounted on the first surface S1 of the wiring substrate 13. The light receiving element 14B is mounted on the first surface S1 of the wiring substrate 13. That is, the light emitting element 14A and the light receiving element 14B are mounted on only the first surface S1 of the wiring substrate 13. Thus, for example, when manufacturing the electronic device 10, while the wiring substrate 13 is supported by the support substrate 70, the light emitting element 14A and the light receiving element 14B are mounted on the wiring substrate 13. Since the mechanical strength of the wiring substrate 13 is increased by the support substrate 70 when mounting the light emitting element 14A and the light receiving element 14B on the wiring substrate 13, the handleability during the manufacturing process is improved.

(2) The wiring substrate 13 is attached along the outer peripheral surface of the support body 11 and folded at the distal ends of the planar portions 21 and 22 and attached along the inner peripheral surfaces of the planar portions 21 and 22. The light emitting element 14A is mounted on the first surface S1 of the mount portion 13A of the wiring substrate 13 attached along the inner peripheral surface of the planar portion 21. The light receiving element 14B is mounted on the first surface S1 of the mount portion 13G of the wiring substrate 13 attached along the inner peripheral surface of the planar portion 22. Thus, even when the light emitting element 14A and the light receiving element 14B are mounted on only the first surface S1 of the wiring substrate 13, the light emitting element 14A and the light receiving element 14B face each other. In the electronic device 10, when the measurement subject T1 is inserted into the receptacle 26, the light emitting element 14A and the light receiving element 14B sandwich the measurement subject T1 and face each other.

(3) All of the electronic components 14 are mounted on only the first surface S1 of the wiring substrate 13. Thus, for example, when manufacturing the electronic device 10, while the wiring substrate 13 is supported by the support substrate 70, all of the electronic components 14 are mounted on the wiring substrate 13. Since the mechanical strength of the wiring substrate 13 is increased by the support substrate 70 when mounting the electronic components 14 on the wiring substrate 13, the handleability during the manufacturing process is improved.

(4) The plates 24B and 25B are arranged at the entrance of the receptacle 26, into which the measurement subject T1 is inserted. The plate 24B cantilevers from the base 24A and extends along the planar portion 21. The plate 25B cantilevers from the base 25A and extends along the planar portion 22. The plates 24B and 25B are configured to elastically deform in a direction (here, the height-wise direction Z) in which the planar portion 21 and the planar portion 22 are arranged facing each other. Thus, for example, when the thickness of the measurement subject T1 is greater than the gap between the plate 24B and the plate 25B and the measurement subject T1 is inserted into the receptacle 26, the plates 24B and 25B elastically deform to widen the gap between the plate 24B and the plate 25B. This allows the measurement subject T1 to be appropriately inserted into the receptacle 26. The elastic deformation of the plates 24B and 25B absorbs variations in the thickness of the measurement subject T1.

(5) The light emitting element 14A is arranged between the inner peripheral surface of the planar portion 21 and the plate 24B. The light receiving element 14B is arranged between the inner peripheral surface of the planar portion 22 and the plate 25B. With this configuration, even when the plates 24B and 25B elastically deform, movement of the light emitting element 14A and the light receiving element 14B caused by the elastic movement is limited. This limits displacement of optical axes of the light emitting element 14A and the light receiving element 14B and allows accurate detection of biometric information of the measurement subject T1.

(6) The antenna 14C is mounted on the first surface S1 of the mount portion 13C of the wiring substrate 13 attached to the outer peripheral surface of the planar portion 21. Also, the antenna 14C is arranged at a position overlapping the plate 24B in plan view. In this configuration, when the measurement subject T1 is inserted into the receptacle 26, the plate 24B, the space (i.e., the accommodation portion 27) between the plate 24B and the planar portion 21, and the planar portion 21 are located between the measurement subject T1 and the antenna 14C. Thus, the distance between the measurement subject T1 and the antenna 14C is relatively increased. This appropriately limits adverse effects on the properties of the antenna 14C produced when the measurement subject T1, that is, a human body having a relatively high electric permittivity, approaches the antenna 14C.

(7) The adhesive 15, which adheres the wiring substrate 13 to the inner peripheral surface of the planar portion 21, is applied to a position that does not overlap the antenna 14C in plan view. Thus, even when the adhesive 15 has a high electric permittivity, adverse effects on the properties of the antenna 14C produced by the adhesive 15 are limited.

(8) The shield pattern 34B located in the bent portions 13B and 13F includes the through holes 34X arranged at given intervals. The planar shape of each through hole 34X includes the corners C1 and C2. This configuration decreases the flexural modulus of the shield pattern 34B and the flexural modulus of the bent portions 13B and 13F as compared to a configuration in which a shield pattern is a solid pattern and does not include a through hole. As a result, the flexibility of the bent portions 13B and 13F is improved.

(9) When the through holes 34X are formed in the shield pattern 34B, the corners C3 and C4 are formed on the shield pattern 34B defined by the through holes 34X. The shield pattern 34B obtains spring-like characteristics from the corners C3 and C4, and a favorable flexibility is obtained from the spring-like characteristics.

(10) The shield pattern 34B includes the supports 44 extending parallel to each other in a direction orthogonal to the bending direction and the joints 45 formed between adjacent ones of the supports 44. The planar shape of each joint 45 includes the corners C3 and C4. In this configuration, the joint 45 has spring-like characteristics, and a favorable flexibility is obtained from the spring-like characteristics.

(11) The supports 44, which have a higher rigidity than the joints 45 including the corners C3 and C4, extend in a direction orthogonal to the bending direction. Thus, interference of the supports 44 with the flexibility of the bent portions 13B and 13F is appropriately limited.

(12) The entirety of the joints 45, which have a lower rigidity than the supports 44 and have spring-like characteristics, extends in the bending direction. This effectively decreases the flexural modulus of the bent portions 13B and 13F and further improves the flexibility of the bent portions 13B and 13F.

(13) In the bent portions 13B and 13F, the through holes 34X and 36X arranged in the shield patterns 34B and 36B that are adjacent to each other in the stacking direction overlap each other in plan view. This allows gas to be readily removed through the through holes 34X and 36X. In other words, the through holes 34X and 36X are used as degassing holes. The through holes 34X and 36X used as degassing holes limit formation of voids in the wiring substrate 13. The degassing hole is a hole used to release gas from the wiring substrate during a process of manufacturing the wiring substrate in which the wiring substrate is heated and the gas is generated.

It should be apparent to those skilled in the art that the foregoing embodiments may be implemented in many other specific forms without departing from the scope of this disclosure. Particularly, it should be understood that the foregoing embodiments may be implemented in the following forms.

The embodiment and the following modified examples may be combined as long as the combined modified examples remain technically consistent with each other.

Figure 15:
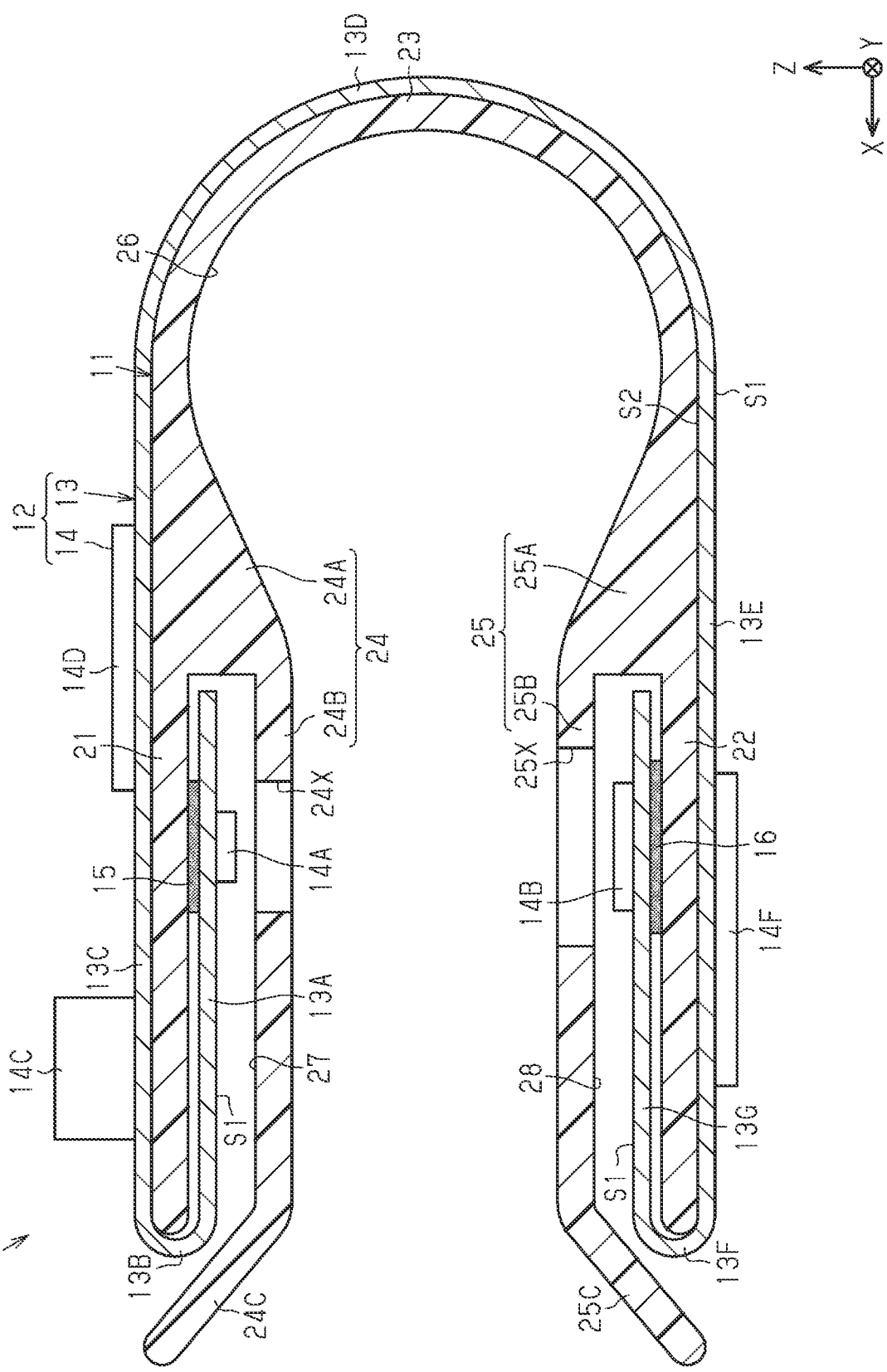
FIGS. 15, 16, and 17 are schematic cross-sectional views illustrating various modified examples of electronic devices.

As illustrated in FIG. 15, the distal ends of the plates 24B and 25B may project outward from the receptacle 26. The distal ends of the plates 24B and 25B may be formed so that the gap between the plate 24B and the plate 25B becomes larger as the distal ends of the plates 24B and 25B extend away from the receptacle 26. That is, the distal end of the plate 24B and the distal end of the plate 25B are separated more from each other at positions farther from the receptacle 26. The distal end of the plate 24B includes, for example, a guide 24C that is inclined toward the planar portion 21 (upward in FIG. 15) at positions farther from the receptacle 26. In the same manner, the distal end of the plate 25B includes, for example, a guide 25C that is inclined toward the planar portion 22 (downward in FIG. 15) at positions farther from the receptacle 26.

In this configuration, when the measurement subject T1 (refer to FIG. 3) is inserted into the receptacle 26, the measurement subject T1 is guided into the receptacle 26 along inclined surfaces of the guides 24C and 25C. This allows the measurement subject T1 to be readily inserted into the receptacle 26 of the electronic device 10. When the electronic device 10 is attached to the measurement subject T1 of an examinee, the attachability is improved.

In the embodiment, the branch 24 may be omitted from the support body 11. Also, the branch 25 may be omitted from the support body 11. Furthermore, the branches 24 and 25 may be omitted from the support body 11.

Figure 16:
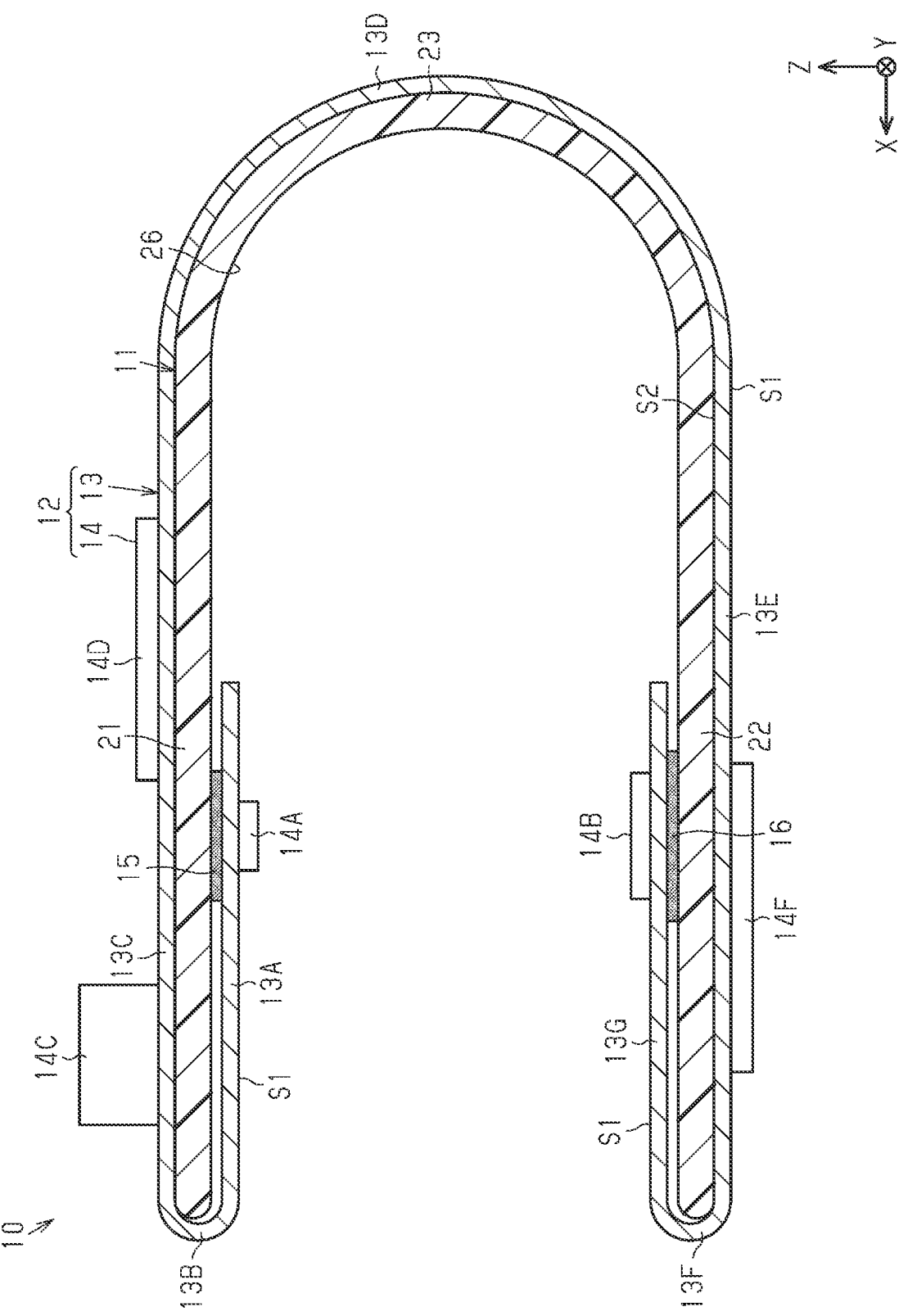

In such a case, as illustrated in FIG. 16, the support body 11 is formed by, for example, the planar portions 21 and 22 and the connecting portion 23. Even in this case, the mount portion 13A covers the inner peripheral surface of the planar portion 21, and the mount portion 13G covers the inner peripheral surface of the planar portion 22. Also, the light emitting element 14A is mounted on the first surface S1 of the mount portion 13A, and the light receiving element 14B is mounted on the first surface S1 of the mount portion 13G to face the light emitting element 14A.

In the embodiment, the connecting portion 23 of the support body 11 is curved as an arc. However, there is no limitation to such a configuration.

Figure 17:
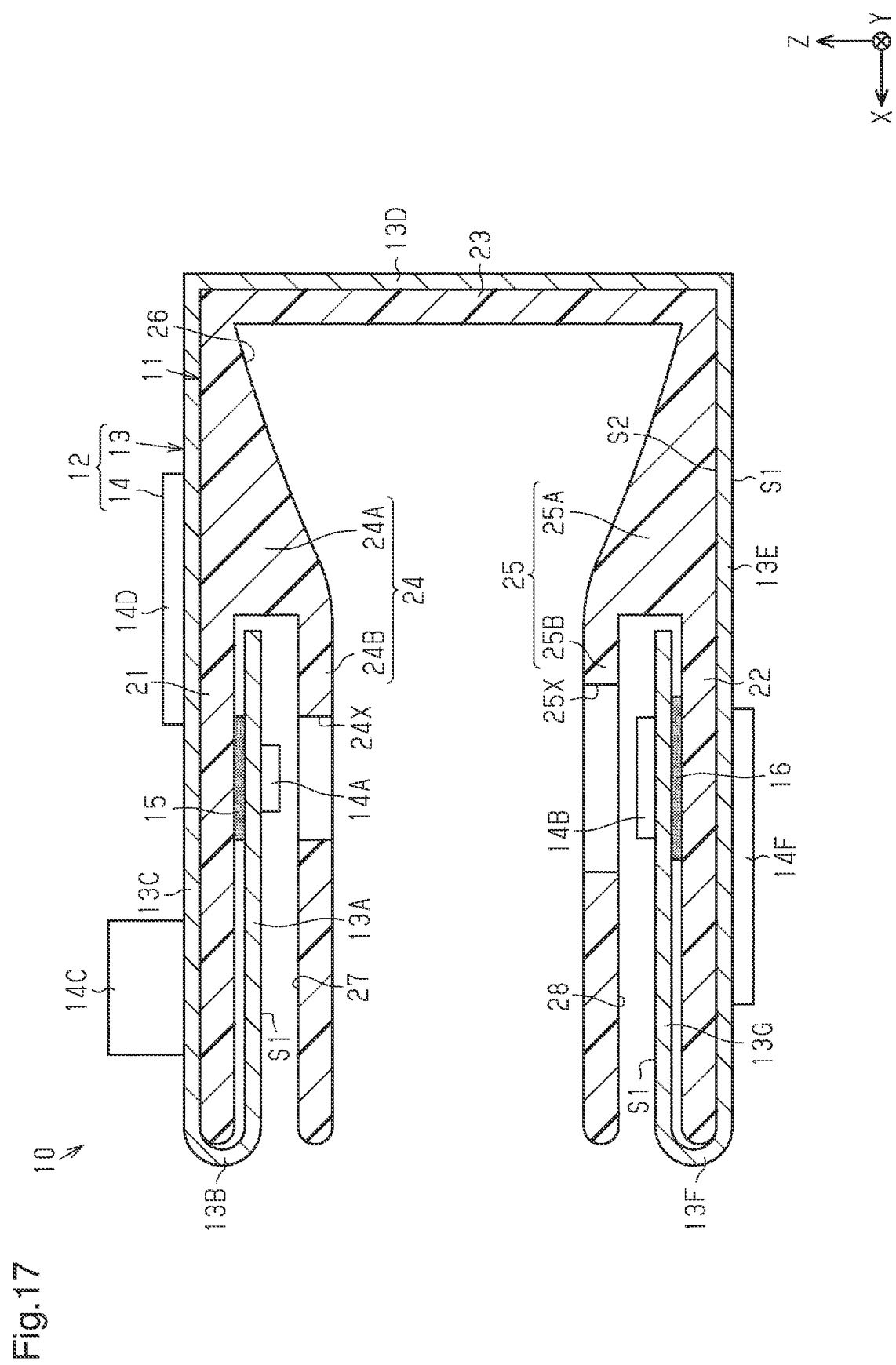

For example, as illustrated in FIG. 17, the connecting portion 23 may extend straight in the height-wise direction Z. In this case, the non-mount portion 13D extends, for example, straight along the connecting portion 23.

In the electronic device 10 of the embodiment, the adhesive 15 is arranged at only a position that overlaps the mount region of the light emitting element 14A in plan view. Instead, for example, the adhesive 15 may be arranged on the entire second surface S2 of the mount portion 13A.

The adhesive 15 of the embodiment may be omitted.

In the electronic device 10 of the embodiment, the adhesive 16 is arranged at only a position that overlaps the mount region of the light receiving element 14B in plan view. Instead, for example, the adhesive 16 may be arranged on the entire second surface S2 of the mount portion 13G.

The adhesive 16 of the embodiment may be omitted.

In the semiconductor device 12 of the embodiment, the number of electronic components 14 and mount positions of the electronic components 14 are not particularly limited. For example, the light emitting element 14A and other electronic components 14 may be mounted on the mount portion 13A. For example, the light receiving element 14B and other electronic components 14 may be mounted on the mount portion 13G. For example, the light receiving element 14B may be mounted on the mount portion 13A, and the light emitting element 14A may be mounted on the mount portion 13G. For example, the electronic component 14 does not have to be mounted on the mount portion 13E. For example, the electronic component 14 may be mounted on the non-mount portion 13D.

In the embodiment, the mounting mode (e.g., flip-chip-mounting, wire-bonding mounting, solder mounting, or combination of these) of the electronic components 14 in the semiconductor device 12 may be appropriately changed.

In the embodiment, the electronic device 10 may include a power supply device. For example, the electronic device 10 may include a battery or the like that supplies power to the controller 50 and the like.

The structure of the shield patterns 34B and 36B located in the bent portions 13B and 13F is not particularly limited. For example, the planar shape of the through holes 34X and 36X is not particularly limited as long as at least one corner is included. For example, the planar shape of the joints 45 is not particularly limited as long as at least one corner is included.

Figure 18:
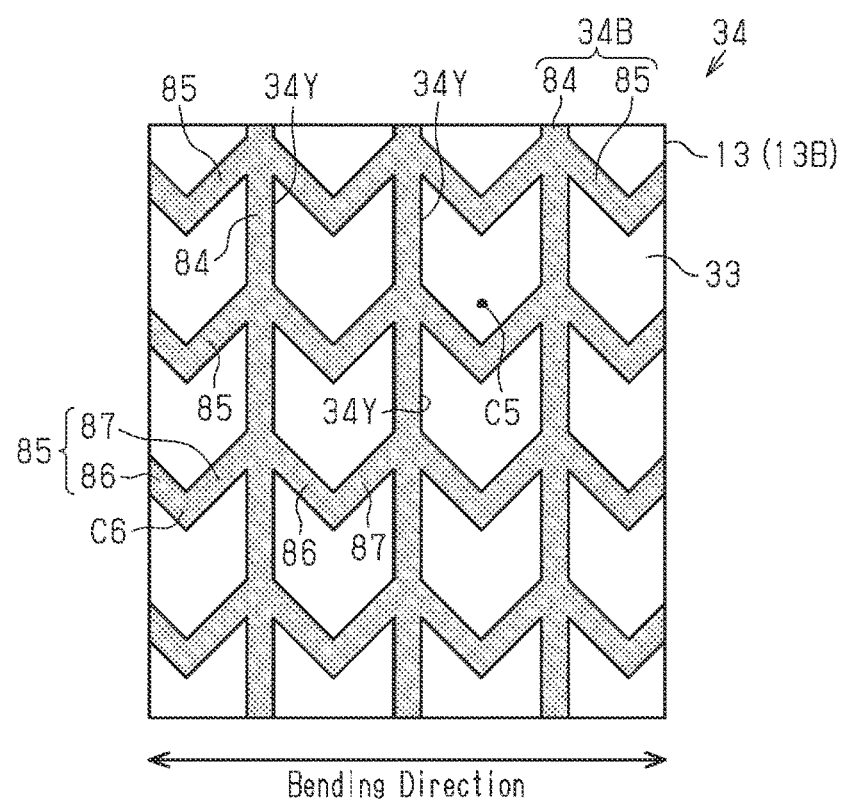
FIGS. 18 and 19 are schematic plan views illustrating various modified examples of shield patterns of a wiring substrate.

For example, as illustrated in FIG. 18, the shield pattern 34B located in the bent portion 13B may include V-shaped through holes 34Y having a planar shape including one corner C5. The through holes 34Y are arranged, for example, at given intervals in the bending direction and also at given intervals in a lateral direction that is orthogonal to the bending direction in plan view.

In the present example, the shield pattern 34B includes supports 84 extending parallel to each other in the lateral direction intersecting the bending direction in plan view and joints 85 formed between adjacent ones of the supports 84 and connecting the adjacent supports 84.

Each support 84 has, for example, a given width and extends straight. The supports 84 are, for example, arranged at given intervals in the bending direction. In the example illustrated in FIG. 18, three supports 84 are arranged. However, the number of supports 84 is not particularly limited. Two supports 84 may be arranged, or four or more supports 84 may be arranged.

The joints 85 are, for example, arranged at given intervals in the lateral direction, which is orthogonal to the bending direction, between adjacent ones of the supports 84. The joints 85 are, for example, arranged at given intervals in the bending direction. In the present example, the joints 85 that are arranged next to one another in the bending direction are located at the same position in the lateral direction. The joints 85 are, for example, the same in planar shape and size. The joints 85 are, for example, arranged in the same direction.

In the present example, the planar shape of each joint 85 is V-shaped and includes one corner C6. That is, the joint 85 includes an extension 86 and an extension 87. The extension 86 extends in a direction intersecting an extension direction of the support 84. The extension 87 extends from an end of the extension 86 in a direction intersecting the extension direction of the support 84 and an extension direction of the extension 86. In the present example, the extension 87 extends in a direction that intersects the extension direction of the support 84 and is orthogonal to the extension direction of the extension 86. That is, in each joint 85 of the present example, the extension 87 is substantially orthogonal to the extension 86. In the joint 85, the corner C6 is formed in the part that connects the extension 86 and the extension 87. For example, in the joint 85, the extension 86 and the extension 87 are located at the same position in the lateral direction. The extension 86 and the extension 87 are, for example, the same in planar shape and size. The extension 86 has an end connected to one of the adjacent supports 84. The extension 87 has an end connected to the other one of the adjacent supports 84. For example, the adjacent supports 84, the extension 86, and the extension 87 are formed continuously and integrally with each other.

As described above, in the shield pattern 34B of the present example, the planar shape of the joint 85 formed between the adjacent supports 84 includes one corner C6. As a result, the joint 85 has spring-like characteristics, and a favorable flexibility is obtained from the spring-like characteristics.

Although the details are not illustrated, the shield pattern 36B located in the bent portions 13B and 13F (refer to FIG. 5) includes through holes having the same planar shape as the through holes 34Y and arranged at the same intervals as the through holes 34Y. For example, through holes formed in the shield patterns 34B and 36B adjacent to each other in the stacking direction overlap in plan view.

In the embodiment, the planar shape of the joint 45 may include three or more corners. For example, the planar shape of the joints 45 may be W-shaped.

In the embodiment, the supports 44 of the shield pattern 34B extend in a direction orthogonal to the bending direction. However, there is no limitation to such a configuration.

Figure 19:
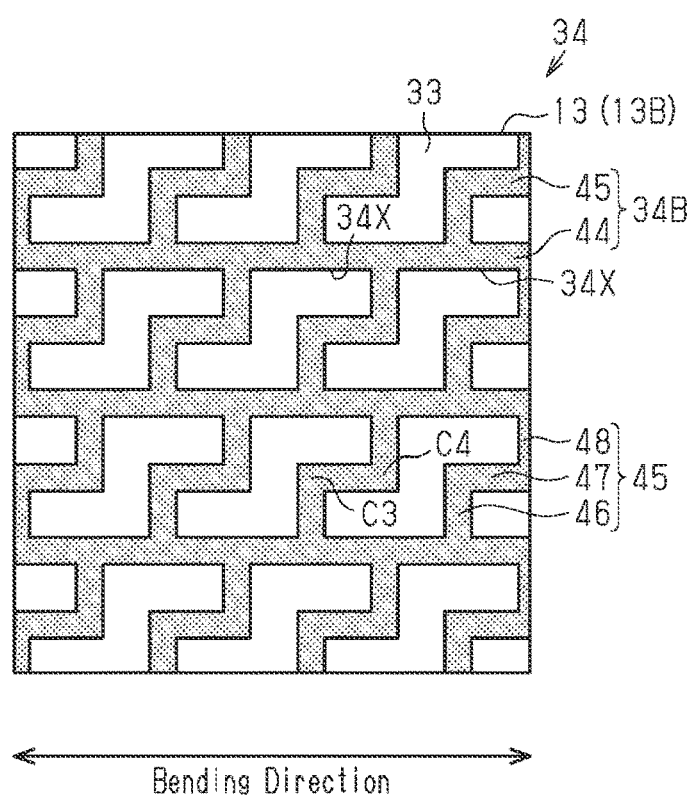

For example, as illustrated in FIG. 19, the supports 44 may extend in the bending direction. In this case, the joints 45 are formed between the supports 44 that are adjacent to each other in the lateral direction, which is orthogonal to the bending direction. The shield pattern 34B illustrated in FIG. 19 has a structure obtained when the shield pattern 34B illustrated in FIG. 6 is rotated ninety degrees to the right (clockwise) in plan view.

In the embodiment, the shield patterns 34B and 36B located in the bent portion 13B have substantially the same planar shape. Instead, for example, the planar shape may differ between the shield patterns 34B and 36B located in the bent portion 13B. For example, the planar shape of the joint 45 may differ between the shield patterns 34B and 36B.

In the embodiment, the through holes 34X and 36X having corners are formed in all of the shield patterns 34B and 36B located in the bent portions 13B and 13F. Instead, the bent portions 13B and 13F may include a shield pattern that does not include a through hole including a corner. For example, the shield patterns 34B and 36B located in the bent portions 13B and 13F, the through holes 34X including corners may be formed in only the shield pattern 34B.

In the embodiment, the number of wiring layers in the wiring substrate 13 is not particularly limited. For example, the number of wiring layers in the bent portions 13B and 13F may be the same as the number of wiring layers in the mount portion 13A.

In the embodiment, the wiring substrate 13 is embodied in a coreless substrate. However, there is no limitation to such a configuration. For example, the wiring substrate 13 may be embodied in a wiring substrate having a core substrate.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to an illustration of the superiority and inferiority of the invention. Although embodiments have been described in detail, it should be understood that various changes, substitutions, and alterations could be made hereto without departing from the scope of this disclosure.

What is claimed is:

1. An electronic device, comprising:
a support body including
a first planar portion and a second planar portion that are arranged facing each other,
a connecting portion connecting a basal end of the first planar portion and a basal end of the second planar portion, and
a receptacle surrounded by the first and second planar portions and the connecting portion;
a wiring substrate attached along an outer peripheral surface of the support body, folded at a distal end of each of the first and second planar portions, and attached along an inner peripheral surface of each of the first and second planar portions, the distal end and the basal end are located at opposite sides of each planar portion;
a light emitting element mounted on a first surface of the wiring substrate at a portion of the wiring substrate attached along the inner peripheral surface of the first planar portion; and
a light receiving element mounted on the first surface of the wiring substrate at a portion of the wiring substrate attached along the inner peripheral surface of the second planar portion so that the light receiving element faces the light emitting element.

2. The electronic device according to claim 1, wherein the support body further includes
a first branch branching from the basal end of the first planar portion and extending parallel to the first planar portion, and
a second branch branching from the basal end of the second planar portion and extending parallel to the second planar portion,
wherein the first branch and the second branch are arranged between the first planar portion and the second planar portion and faced toward each other,
the light emitting element is arranged between the inner peripheral surface of the first planar portion and the first branch, and
the light receiving element is arranged between the inner peripheral surface of the second planar portion and the second branch.

3. The electronic device according to claim 2, wherein the first branch includes a first through hole extending through the first branch at a position overlapping the light emitting element in plan view, and
the second branch includes a second through hole extending through the second branch at a position overlapping the light receiving element in plan view.

4. The electronic device according to claim 2, wherein a distal end of the first branch and a distal end of the second branch project outward from the receptacle, and
a gap between the first branch and the second branch becomes larger as the distal ends of the first and second branches extend away from the receptacle.

5. The electronic device according to claim 2, further comprising:
an antenna mounted on the first surface of the wiring substrate at a portion of the wiring substrate attached to an outer peripheral surface of the first planar portion,
wherein the antenna is arranged at a position that overlaps the first branch in plan view.

6. The electronic device according to claim 5, wherein the wiring substrate is adhered to the inner peripheral surface of the first planar portion by an adhesive, and the adhesive is arranged at a position that does not overlap the antenna in plan view.

7. The electronic device according to claim 1, further comprising:
a first base projecting inside the receptacle from the basal end of the first planar portion;
a first plate cantilevering from the first base and extending along the first planar portion, the first plate being spaced apart from the first planar portion in a first direction in which the first planar portion and the second planar portion are arranged facing each other;
a second base projecting inside the receptacle from the basal end of the second planar portion; and
a second plate cantilevering from the second base and extending along the second planar portion, the second plate being spaced apart from the second planar portion in the first direction, wherein
the first plate and the second plate are configured to elastically deform in the first direction,
the light emitting element is arranged between the inner peripheral surface of the first planar portion and the first plate, and
the light receiving element is arranged between the inner peripheral surface of the second planar portion and the second plate.

8. The electronic device according to claim 7, wherein the first plate includes a first through hole extending through the first plate at a position overlapping the light emitting element in plan view, and
the second plate includes a second through hole extending through the second plate at a position overlapping the light receiving element in plan view.

9. The electronic device according to claim 7, wherein a distal end of the first plate and a distal end of the second plate project outward from the receptacle, and
a gap between the first plate and the second plate becomes larger as the distal ends of the first and second plates extend away from the receptacle.

10. The electronic device according to claim 7, further comprising:
an antenna mounted on the first surface of the wiring substrate at a portion of the wiring substrate attached to an outer peripheral surface of the first planar portion,
wherein the antenna is arranged at a position that overlaps the first plate in plan view.

11. The electronic device according to claim 10, wherein the wiring substrate is adhered to the inner peripheral surface of the first planar portion by an adhesive, and
the adhesive is arranged at a position that does not overlap the antenna in plan view.

12. The electronic device according to claim 1, further comprising:
an electronic component mounted on the first surface of the wiring substrate at a portion of the wiring substrate attached to the outer peripheral surface of the support body.

13. The electronic device according to claim 1, wherein the wiring substrate includes a bent portion arranged at the distal end of each of the first and second planar portions,
the wiring substrate has a structure in which wiring layers and insulation layers are alternately stacked,
at least one of the wiring layers includes a shield pattern,
the shield pattern located in the bent portion includes through holes arranged at a given interval, and
each of the through hole has a planar shape including at least one corner.

14. The electronic device according to claim 13, wherein the shield pattern located in the bent portion includes
- supports extending parallel to each other in a direction orthogonal to a bending direction of the bent portion, and
- a joint located between adjacent ones of the supports and connecting the adjacent ones of the supports, and the joint has a crank-shaped planar shape having two corners.

15. The electronic device according to claim 1, wherein the connecting portion is curved as an arc.

* * * * *